US011754565B2

United States Patent
Cetlin et al.

(10) Patent No.: US 11,754,565 B2
(45) Date of Patent: Sep. 12, 2023

(54) METHODS AND KITS FOR QUANTIFYING THE REMOVAL OF MOCK VIRUS PARTICLES FROM A PURIFIED SOLUTION

(71) Applicant: MockV Solutions, Rockville, MD (US)

(72) Inventors: David Cetlin, Potomac, MD (US); Arun Dhar, Tucson, AZ (US)

(73) Assignee: MOCKV SOLUTIONS LLC, Rockville, MD (US)

( * ) Notice: Subject to any disclaimer, the term of this patent is extended or adjusted under 35 U.S.C. 154(b) by 0 days.

(21) Appl. No.: 16/386,327

(22) Filed: Apr. 17, 2019

(65) Prior Publication Data

US 2019/0353656 A1  Nov. 21, 2019

Related U.S. Application Data

(63) Continuation of application No. 15/456,487, filed on Mar. 11, 2017, now Pat. No. 10,309,963, which is a continuation of application No. 14/481,364, filed on Sep. 9, 2014, now Pat. No. 9,632,087.

(60) Provisional application No. 61/875,729, filed on Sep. 10, 2013.

(51) Int. Cl.
| | | |
|---|---|---|
| G01N 33/569 | (2006.01) | |
| A61K 39/23 | (2006.01) | |
| A61K 39/12 | (2006.01) | |
| A61K 39/00 | (2006.01) | |
| A61K 39/21 | (2006.01) | |
| C12Q 1/70 | (2006.01) | |

(52) U.S. Cl.
CPC ....... *G01N 33/56983* (2013.01); *A61K 39/12* (2013.01); *A61K 39/23* (2013.01); *A61K 39/21* (2013.01); *A61K 2039/5258* (2013.01); *C12N 2740/10023* (2013.01); *C12N 2750/14023* (2013.01); *C12Q 1/701* (2013.01); *C12Q 2600/158* (2013.01); *G01N 2333/015* (2013.01); *G01N 2333/15* (2013.01)

(58) Field of Classification Search
CPC ....... G01N 33/56983; G01N 2333/015; A61K 39/23; C12N 2750/14023
See application file for complete search history.

(56) References Cited

U.S. PATENT DOCUMENTS

| | | | | |
|---|---|---|---|---|
| 5,173,399 | A * | 12/1992 | Mehta ................ | C07K 16/1054 435/5 |
| 5,714,316 | A | 2/1998 | Weiner et al. | |
| 5,814,442 | A | 9/1998 | Natarajan et al. | |
| 5,905,040 | A | 5/1999 | Mazzara et al. | |
| 7,763,260 | B2 * | 7/2010 | Virgin ..................... | C12N 7/00 424/216.1 |
| 9,632,087 | B2 | 4/2017 | Cetlin et al. | |
| 2003/0108864 | A1 | 6/2003 | Liu et al. | |
| 2003/0129744 | A1 | 7/2003 | Schlapp et al. | |
| 2004/0002058 | A1 | 1/2004 | Cosenza | |
| 2006/0281128 | A1 | 12/2006 | Lu et al. | |
| 2007/0184068 | A1 | 8/2007 | Renner et al. | |
| 2008/0132688 | A1 | 6/2008 | Zhou | |
| 2010/0136025 | A1 | 6/2010 | Hickman et al. | |
| 2010/0297604 | A1 | 11/2010 | Li et al. | |
| 2011/0177539 | A1 | 7/2011 | Sutton et al. | |
| 2011/0243986 | A1 | 10/2011 | Deng et al. | |
| 2012/0088228 | A1 | 4/2012 | Asher et al. | |
| 2013/0273109 | A1 * | 10/2013 | Settembre ............... | A61P 15/00 424/233.1 |
| 2015/0072339 | A1 | 3/2015 | Cetlin et al. | |

FOREIGN PATENT DOCUMENTS

JP    2011512151 A    4/2011

OTHER PUBLICATIONS

Kuck, D., et al., 2007, Development of AAV serotype-specific ELISAs using novel monclonal antibodies, J. Virol. Meth. 140:17-24.*
Yang, L., et al., Jul. 2012, HIV-1 virus-like particles produced by stably transfected *Drosophila* S2 cells: a desirable vaccine component, J. Virol. 86(14):7662-7676.*
Livingston, R. S., et al., Sep. 2002, Serodiagnosis of mice minute virus and mouse parvovirus infections in mice by enzyme-linked immunosorbent assay with baculovirus-expressed recombinant VP2 proteins, Clin. Diag. Lab. Immunol. 9(5):1025-1031.*
Andersson, I. et al. "Validation Study for the Removal/Inactivation of Viruses During a Chromatographic Purification Process for Albumin and IgG", Presentation at the 24th Conference of the International Society of Blood Transfusion in Makuhari, Japan. Amersham Biosciences, pp. 1-5, (1996).
Anonymous, "Process Validation in Manufacturing of Biopharmaceuticals", in Biotechnology and Bioprocessing Series, vol. 35, Chapter 1, pp. 1-9, (2012).
Aranha et al., "Virus Safety of Biopharmaceuticals: Absence of Evidence is Not Evidence of Absence", Contract Pharma, pp. 82-87, (2011).
Aranha, H. and Forbes, S., "Viral Clearance Strategies for Biopharmaceutical Safety—Part II: A Multifaceted Approach to Process Validation", Pharmaceutical Technology, Biotech Trends, pp. 26-42, (2001).

(Continued)

*Primary Examiner* — Jeffrey S Parkin
(74) *Attorney, Agent, or Firm* — Kilpatrick Townsend & Stockton LLP

(57) ABSTRACT

The present invention relates to a method of quantifying the amount of Mock Virus Particles (MVP) removed from a solution as a result of processing that solution through a purification technique. This method involves the steps of adding MVP to a solution, processing the solution through a purification technique, quantifying the amount of MVP removed from the solution. The present invention also relates to a kit that can be used in conjunction with the method. This kit will comprise at least one stock solution of MVP and at least one quantification solution.

8 Claims, 4 Drawing Sheets

Specification includes a Sequence Listing.

(56) References Cited

OTHER PUBLICATIONS

Burnouf, T. et al., "Place of Nanofiltration for Assuring Viral Safety of Biologicals", Current Nanoscience, vol. 1 pp. 189-201, (2005).
Caballero et al., "Rotavirus Virus-Like Particles as Surrogates in Environmental Persistence and Inactivation Studies", Applied and Environmental Microbiology, vol. 70, No. 7, pp. 3904-3909, (2004).
Cipriano et al., "Effectiveness of Various Processing Steps for Viral Clearance of Therapeutic Proteins: Database Analyses of Commonly Used Steps", Methods of Mol. Biol., vol. 899, pp. 277-292, (2012).
Communication pursuant to Article 94(3) EPC dated Mar. 23, 2018.
Connell-Crowley, L. et al., "Using High Throughput Screening to Define Virus Clearance by Chromatography Resins", Biotechnology and Bioengineering, vol. 110, No. 7, pp. 1984-1994, (2013).
Curtis, S. et al., "Generic/Matrix Evaluation of SV40 Clearance by Anion Exchange Chromatography in Flow-Through Mode", Biotechnology and Bioengineering, vol. 84, No. 2, pp. 179-186, (2003).
Darling, A. "Validation of Biopharmaceutical Purification Processes for Virus Clearance Evaluation", Molecular Biotechnology, vol. 21, pp. 57-83, (2002).
De Wit, C., "Real-Time Quantitative PCR for Retrovirus-Like Particle Quantification in CHO Cell Culture", Biologicals, vol. 20, pp. 137-143, 28, Elsevier, London, (2000).
EMEA European Medicines Agency, "Guideline on Virus Safety Evaluation of Biotechnological Investigational Medicinal Products", European Medicines Agency, EMEA/CHMP/BWP/398498/2005, London, pp. 1-9, (2008).
EMEA European Medicines Agency, "ICH Topic Q 5 A (R1) Note for Guidance on Quality of Biotechnology Products, Viral Safety Evaluation of Biotechnology Products Derived from Cell Lines of Human or Animal Origin", CPMP/ICH/295/95, London, pp. 1-29, (1997).
EMEA The European Agency for the Evaluation of Medicinal Products, Human Medicines Evaluation Unit, "Note for Guidance on Virus Validation Studies: The Design, Contribution and Interpretation of Studies Validating the Inactivation and Removal of Viruses", 1996, European Medicines Agency, London, pp. 1-14, (1996).
Extended European Search Report dated Mar. 28, 2017, received in EP 14 843 784.1.
Grasso, S. and Santi, L., "Viral Nanoparticles as Macromolecular Devices for New Therapeutic and Pharmaceutical Approaches", International Journal of Physiology, Pathophysiology and Pharmacology, vol. 2, No. 2, pp. 161-178, (2010).
Grgacie et al., "Virus-Like Particles: Passport to Immune Recognition", Methods, vol. 40, pp. 60-65 (2006).
Grimm, D. et al., "Titration of AAV-2 Particles Via a Novel Capsid ELISA: Packaging of Genomes Can Limit Production of Recombinant AAV-2", Gene Therapy, vol. 6, No. 7, pp. 1322-1330, (1999).
Henzier, H.-J. and Kaiser, K., "Avoiding Viral Contamination in Biotechnological and Pharmaceutical Processes", Nature Biotechnology, vol. 16, pp. 1077-1079, (1998).
International Conference on Harmonization of Technical Requirements for Registration of Pharmaceuticals for Human Use, ICH Harmonised Tripartite Guideline, Viral Safety Evaluation of Biotechnology Products Derived from Cell Lines of Human or Animal Origin Q5A(R1), Current Step 4 Version, pp. 1-31, (1999).
International Search Report and Written Opinion received PCT/IB14/64352 dated Mar. 16, 2015.
Kajigaya, S., et al., "Self-Assembled B19 Parvovirus Capsids, Produced in a Baculovirus System, are Antigenically and Immunogenically Similar to Native Virions", Proceedings of the National Academy of Sciences USA, vol. 88, pp. 4646-4650, (1991).
Khan, et al., "Filter Preconditioning Enables Representative Scaled-Down Modelling of Filter Capacity and Viral Clearance by Mitigating the Impact of Virus Spike Impurities", Biotechnology Applied Biochemistry, vol. 52, pp. 293-301, (2009).
Kratz, P. et al., Native Display of Complete Foreign Protein Domains on the Surface of Hepatitis B Virus Capsids, Proceedings of the National Academy of Sciences, vol. 96, pp. 1915-1920, (1999).
Kuck, D. et al., "Development of AAV Serotype-Specific ELISAs Using Novel Monoclonal Antibodies", Journal of Virological Methods, vol. 140, pp. 17-24, (2007).
Kundu, A. et al., "Evaluation of Viral Clearance in Purification Processes" Process Scale Bioseparations for the Biopharmaceutical Industry, 2007, 419-448, N.A., Taylor & Francis Group, United Kingdom.
Livingston, R. et al., "Serodiagnosis of Mice Minute Virus and Mouse Parvovirus Infections in Mice by Enzyme-Linked Immunosorbent Assay with Baculovirus-Expressed Recombinant VP2 Proteins", Clinical Diagnostic Laboratory Immunology, vol. 9, No. 5, pp. 1025-1031, (2002).
Lute, S. et al., "Characterization of Coliphage PR772 and Evaluation of Its Use for Virus Filter Performance Testing", Applied and Environmental Microbiology, vol. 70, No. 8, pp. 4864-4871, (2004).
Maerz, H. et al., "Improved Removal of Viruslike Particles from Purified Monoclonal Antibody IgM Preparation Via Virus Filtration", Nature Biotechnology, vol. 14, pp. 651-652, (1996).
Miesegaes et al., "Analysis of Viral Clearance Unit Operations for Monoclonal Antibodies", Biotech. Bioengin, vol. 106, No. 2, pp. 238-246 (2010).
Office of Action Japanese and translation dated Aug. 27, 2018, Application No. 2016-539674.
Peabody, D., "A Viral Platform for Chemical Modification and Multivalent Display", Journal of Nanobiotechnology, vol. 1, No. 5, pp. 1-8, (2003).
Shi, L. et al., "Real Time Quantitative PCR as a Method to Evaluate Xenotropic Murine Leukemia Virus Removal During Pharmaceutical Protein Purification", Biotechnology and Bioengineering, vol. 87, No. 7, pp. 884-896, (2004).
Valera, et al., "Application of Multivirus Spike Approach for Viral Clearance Evaluation", Biotechnology and Bioengineering, vol. 84, No. 6, pp. 714-722, (2003).
Wang, H. and Middelberg, A., "Non-lnfectious Virus-Like Particles for the Validation of Membrane Integrity and Column Performance in Bioprocessing", Food and Bioproducts Processing, vol. 98, pp. 327-332, (2016).
Willkommen et al., "Viral Clearance Integration (Session IV): General Trends, Bracketing, QbD, Virus Preparation Quality Attributes", PDA Journal of Pharmaceutical Science and Technology, vol. 68, pp. 66-82, (2014).
Wistuba, A. et al., "Subcellular Compartmentalization of Adeno-Associated Virus Type 2 Assembly", Journal of Virology, vol. 71, No. 2, pp. 1341-1352, (1997).
Wobus, C. et al., "Monoclonal Antibodies Against the Adeno-Associated Virus Type 2 (AAV-2) Capsid: Epitope Mapping and Identification of Capsid Domains involved in AAV-2-Cell Interaction and Neutralization of AAV-2 Infection", Journal of Virology, vol. 74, No. 19, pp. 9281-9293, (2000).
Zhang, M. et al., "A Novel, Q-PCR Based Approach to Measuring Endogenous Retroviral Clearance by Capture Protein A Chromatography", Biotechnology and Bioengineering, vol. 102, No. 5, pp. 1438-1447, (2009).
Zhao, X., et al., "Evaluation of Viral Removal by Nanofiltration Using Teal-Time Quantitative Polymerase Chain Reaction," Biotchnol. Appl. Biochem. 47:97-104 (2007).
Zoon, C., "Points to Consider in the Manufacture and Testing of Monoclonal Antibody Products for Human Use", U.S. Department of Health and Human Services, Food and Drug Administration, Center for Biologies Evaluation and Research, pp. 1-50, (1997).
Australian Office Action dated Oct. 31, 2019 received in corresponding AU Application 2014320015.
Hendrickson, Edwin R. et al. "High sensitivity multianalyte immunoassay using covalent DNA-labeled antibodies and polymerase chain reaction," Nucleic Acids Research, 1995, vol. 23, No. 3, pp. 522-529—8 pages.
Adler Michael et al. "Novel Strategies and Tools for Enhanced Sensitivity in Routine Biomolecule Analytics", Current Pharmaceutical Analysis, Nov. 2009, 5, pp. 390-407—18 pages.
Lind Kristina et al. "Development and evaluation of three real-time immuno-PCR assemblages for quantification of PSA", Journal of Immunological Methods 304 (2005) 107-116—10 pages.

(56) References Cited

OTHER PUBLICATIONS

Mehta Promod K. et al. "Detection of potential microbial antigens by immuno-PCR (PCR-amplified immunoassay)", Journal of Medical Microbiology, 2014, vol. 63, pp. 627-641—15 pages.
GenBank Accession No. X02481.1, National Center for Biotechnology Information, Jul. 26, 2016, 3 pages.
Hernando Eva, et al., "Biochemical and physical characterization of parvovirus minute virus of mice virus-like particles", Virology. Feb. 15, 2000; 267(2), pp. 299-309.
AU2021200484, "First Examination Report", dated Jul. 19, 2022, 5 pages.
Grimm, et al., "Titration of AAV-2 Particles via a Novel Capsid Elisa: Packaging of Genomes Can Limit Production of Recombinant AAV-2", Gene therapy, vol. 6, No. 7, Jul. 1999, pp. 1322-1330.
Kuck, et al., "Development of AAV Serotype-Specific ELISAs Using Novel Monoclonal Antibodies", Journal of Virological Methods, vol. 140, Nos. 1-2, Mar. 2007, pp. 17-24.
Wistuba, et al., "Subcellular Compartmentalization of Adeno-Associated Virus Type 2 Assembly", Journal of Virology, vol. 71, No. 2, Feb. 1997, pp. 1341-1352.

* cited by examiner

SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Trp Ser His Pro Gln Phe Glu Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Asp Tyr Lys Asp Asp Asp Lys
1               5

<210> SEQ ID NO 3
<211> LENGTH: 6
<212> TYPE: PRT
<213> ORGANISM: Artificial
<220> FEATURE:
<223> OTHER INFORMATION: Synthetic

<400> SEQUENCE: 3

His His His His His His
1               5

<210> SEQ ID NO 4
<211> LENGTH: 1764
<212> TYPE: DNA
<213> ORGANISM: Minute Virus of Mice

<400> SEQUENCE: 4

```
atgagtgatg gcaccagcca acctgacagc ggaaacgctg tccactcagc tgcaagagtt      60
gaacgagcag ctgacggccc tggaggctct ggggtgggg gctctggcgg gggtgggt      120 ggtgtttcta ctgggtctta tgataatcaa acgcattata gattcttggg tgacggctgg      180
gtagaaatta ctgcactagc aactagacta gtacatttaa acatgcctaa atcagaaaac      240
tattgcagaa tcagagttca caatacaaca gacacatcag tcaaaggcaa catggcaaaa      300
gatgatgctc atgagcaaat ttggacacca tggagcttgg tggatgctaa tgcttgggga      360
gtttggctcc agccaagtga ctgcaatac atttgcaaca ccatgagcca gcttaacttg      420
gtatcacttg atcaagaaat attcaatgta gtgctgaaaa ctgttacaga gcaagactta      480
```

```
ggaggtcaag ctataaaaat atacaacaat gaccttacag cttgcatgat ggttgcagta    540
gactcaaaca acattttgcc atacacacct gcagcaaact caatggaaac acttggtttc    600 taccctgga aaccaaccat agcatcacca tacaggtact atttttgcgt tgacagagat    660
ctttcagtga cctacgaaaa tcaagaaggc acagttgaac ataatgtgat gggaacacca    720
aaaggaatga attctcaatt ttttaccatt gagaacacac aacaaatcac attgctcaga    780
acaggggacg aatttgccac aggtacttac tactttgaca caaattcagt taaactcaca    840
cacacgtggc aaaccaaccg tcaacttgga cagcctccac tgctgtcaac ctttcctgaa    900
gctgacactg atgcaggtac acttactgct caagggagca gacatggaac aacacaaatg    960
ggggttaact gggtgagtga agcaatcaga accagacctg ctcaagtagg attttgtcaa   1020
ccacacaatg actttgaagc cagcagagct ggaccatttg ctgccccaaa agttccagca   1080
gatattactc aaggagtaga caaagaagcc aatggcagtg ttagatacag ttatggcaaa   1140
cagcatggtg aaaattgggc ttcacatgga ccagcaccag agcgctacac atgggatgaa   1200
acaagctttg gttcaggtag agacaccaaa gatggtttta ttcaatcagc accactagtt   1260
gttccaccac cactaaatgg cattcttaca aatgcaaacc ctattgggac taaaaatgac   1320
attcattttt caaatgtttt taacagctat ggtccactaa ctgcattttc acacccaagt   1380
cctgtatacc ctcaaggaca aatatgggac aaagaactag atcttgaaca caaacctaga   1440
cttcacataa ctgctccatt tgtttgtaaa aacaatgcac ctggacaaat gttggttaga   1500
ttaggaccaa acctaactga ccaatatgat ccaaacggag ccacactttc tagaattgtt   1560
acatacggta catttttctg gaaaggaaaa ctaaccatga gagcaaaact tagagctaac   1620
accacttgga acccagtgta ccaagtaagt gctgaagaca atggcaactc atacatgagt   1680
gtaactaaat ggttaccaac tgctactgga aacatgcagt ctgtgccgct tataacaaga   1740
cctgttgcta gaaatactta ctaa                                          1764
```

```

<210> SEQ ID NO 5
<211> LENGTH: 1764
<212> TYPE: DNA
<213> ORGANISM: Artificial Sequence
<220> FEATURE:
<223> OTHER INFORMATION: Modified from Minute Virus of Mice

<400> SEQUENCE: 5
atgtctgatg gcacttcaca accggattct ggaaacgctg ttcactcggc tgctagggtg     60
gaaagggctg ctgatggacc tggcggatcc ggtggaggag gttctggtgg aggtggagtc    120
ggagtttcca ctggttctta cgacaaccag acacactacc gtttcctggg cgatggatgg    180
gtcgagatca ccgctctcgc cactcgcttg gttcacctga acatgcctaa gtcggaaaac    240
tactgccgta tccgcgttca caacaccact gacacctctg tgaagggtaa catggctaag    300
gacgatgccc acgagcaaat ctggactcct tggagcttgg tggacgctaa cgcctggggc    360
gtttggctgc agccatcaga ttggcaatac atctgtaaca ccatgtcgca gctcaacttg    420
gtctccctgg accaagaaat cttcaacgtg gtcctcaaga ccgtgactga acaggacttg    480
ggaggtcaag ctatcaagat ttacaacaac gacctcaccg cttgcatgat ggtggccgtc    540
gattctaaca acatcttgcc ttacacccca gctgccaaca gcatggagac tctgggtttc    600
tacccgtgga agcccaccat cgcctcacct taccgttact acttctgtgt tgaccgcgat    660
ctgtcggtga cctacgagaa ccaggaaggc actgtggaac acaacgtcat gggcacccca    720
```

-continued

```
aagggaatga actcccaatt cttcacaatc gagaacaccc agcaaatcac tctgctcagg    780
acaggcgacg agttcgctac aggaacctac tacttcgata ctaacagcgt gaagctcact    840
cacacatggc agacaaacag acagttgggt caaccccctt tgctgtcaac attccctgag    900
gctgacaccg atgccggcac cctgactgct cagggttcca ggcacggcac aacccaaatg    960
ggagttaact gggtgtctga ggctatcagg accagaccgg cccaagtggg attctgccaa   1020
ccccacaacg acttcgaggc ttcccgtgct ggtccattcg ctgctcctaa ggtcccagct   1080
gacatcactc agggagttga taaggaggcc aacggttcag tgcgctactc gtacggaaag   1140
caacacggtg aaaactgggc tagccacggc cctgctccag agaggtacac ctgggacgaa   1200
actagcttcg gttcaggcag agacaccaag gatggattca tccagtctgc tccgctggtt   1260
gtgccaccgc ccctgaacgg tatcctcaca acgccaacc ctatcggcac caagaacgac    1320
atccacttca gcaacgtctt caactcatac ggtccactga ccgctttctc gcacccatcc   1380
ccagtgtacc cacagggaca aatctgggac aaggagctgg atctcgaaca caagcctcgc   1440
ctccacatca ctgctccatt cgtctgtaag aacaacgctc caggacagat gctcgtgagg   1500
ttgggaccta acctgacaga ccaatacgat ccaaacggcg ctaccctctc cagaatcgtc   1560
acttacggta cattcttctg gaagggcaag ttgaccatgc gtgctaagct gcgcgccaac   1620
actacatgga acccagtcta ccaggttttcc gccgaggaca acggaaactc ttacatgagc   1680
gtgactaagt ggctccccac agctaccggt aacatgcaat ctgtgccgtt gatcactagg   1740
cccgtcgcca gaaacacata ctaa                                          1764
```

<210> SEQ ID NO 6
<211> LENGTH: 587
<212> TYPE: PRT
<213> ORGANISM: Minute Virus of Mice

<400> SEQUENCE: 6

```
Met Ser Asp Gly Thr Ser Gln Pro Asp Ser Gly Asn Ala Val His Ser
1               5                   10                  15

Ala Ala Arg Val Glu Arg Ala Ala Asp Gly Pro Gly Gly Ser Gly Gly
            20                  25                  30

Gly Gly Ser Gly Gly Gly Gly Val Gly Val Ser Thr Gly Ser Tyr Asp
        35                  40                  45

Asn Gln Thr His Tyr Arg Phe Leu Gly Asp Gly Trp Val Glu Ile Thr
    50                  55                  60

Ala Leu Ala Thr Arg Leu Val His Leu Asn Met Pro Lys Ser Glu Asn
65                  70                  75                  80

Tyr Cys Arg Ile Arg Val His Asn Thr Thr Asp Thr Ser Val Lys Gly
                85                  90                  95

Asn Met Ala Lys Asp Asp Ala His Glu Gln Ile Trp Thr Pro Trp Ser
            100                 105                 110

Leu Val Asp Ala Asn Ala Trp Gly Val Trp Leu Gln Pro Ser Asp Trp
        115                 120                 125

Gln Tyr Ile Cys Asn Thr Met Ser Gln Leu Asn Leu Val Ser Leu Asp
    130                 135                 140

Gln Glu Ile Phe Asn Val Val Leu Lys Thr Val Thr Glu Gln Asp Leu
145                 150                 155                 160

Gly Gly Gln Ala Ile Lys Ile Tyr Asn Asn Asp Leu Thr Ala Cys Met
                165                 170                 175

Met Val Ala Val Asp Ser Asn Asn Ile Leu Pro Tyr Thr Pro Ala Ala
            180                 185                 190
```

Asn Ser Met Glu Thr Leu Gly Phe Tyr Pro Trp Lys Pro Thr Ile Ala
            195                 200                 205

Ser Pro Tyr Arg Tyr Tyr Phe Cys Val Asp Arg Asp Leu Ser Val Thr
    210                 215                 220

Tyr Glu Asn Gln Glu Gly Thr Val Glu His Asn Val Met Gly Thr Pro
225                 230                 235                 240

Lys Gly Met Asn Ser Gln Phe Phe Thr Ile Glu Asn Thr Gln Gln Ile
                245                 250                 255

Thr Leu Leu Arg Thr Gly Asp Glu Phe Ala Thr Gly Thr Tyr Tyr Phe
                260                 265                 270

Asp Thr Asn Ser Val Lys Leu Thr His Thr Trp Gln Thr Asn Arg Gln
            275                 280                 285

Leu Gly Gln Pro Pro Leu Leu Ser Thr Phe Pro Glu Ala Asp Thr Asp
        290                 295                 300

Ala Gly Thr Leu Thr Ala Gln Gly Ser Arg His Gly Thr Thr Gln Met
305                 310                 315                 320

Gly Val Asn Trp Val Ser Glu Ala Ile Arg Thr Arg Pro Ala Gln Val
                325                 330                 335

Gly Phe Cys Gln Pro His Asn Asp Phe Glu Ala Ser Arg Ala Gly Pro
                340                 345                 350

Phe Ala Ala Pro Lys Val Pro Ala Asp Ile Thr Gln Gly Val Asp Lys
            355                 360                 365

Glu Ala Asn Gly Ser Val Arg Tyr Ser Tyr Gly Lys Gln His Gly Glu
        370                 375                 380

Asn Trp Ala Ser His Gly Pro Ala Pro Glu Arg Tyr Thr Trp Asp Glu
385                 390                 395                 400

Thr Ser Phe Gly Ser Gly Arg Asp Thr Lys Asp Gly Phe Ile Gln Ser
                405                 410                 415

Ala Pro Leu Val Val Pro Pro Leu Asn Gly Ile Leu Thr Asn Ala
            420                 425                 430

Asn Pro Ile Gly Thr Lys Asn Asp Ile His Phe Ser Asn Val Phe Asn
        435                 440                 445

Ser Tyr Gly Pro Leu Thr Ala Phe Ser His Pro Ser Pro Val Tyr Pro
    450                 455                 460

Gln Gly Gln Ile Trp Asp Lys Glu Leu Asp Leu Glu His Lys Pro Arg
465                 470                 475                 480

Leu His Ile Thr Ala Pro Phe Val Cys Lys Asn Asn Ala Pro Gly Gln
                485                 490                 495

Met Leu Val Arg Leu Gly Pro Asn Leu Thr Asp Gln Tyr Asp Pro Asn
            500                 505                 510

Gly Ala Thr Leu Ser Arg Ile Val Thr Tyr Gly Thr Phe Phe Trp Lys
        515                 520                 525

Gly Lys Leu Thr Met Arg Ala Lys Leu Arg Ala Asn Thr Thr Trp Asn
    530                 535                 540

Pro Val Tyr Gln Val Ser Ala Glu Asp Asn Gly Asn Ser Tyr Met Ser
545                 550                 555                 560

Val Thr Lys Trp Leu Pro Thr Ala Thr Gly Asn Met Gln Ser Val Pro
                565                 570                 575

Leu Ile Thr Arg Pro Val Ala Arg Asn Thr Tyr
            580                 585

<210> SEQ ID NO 7
<211> LENGTH: 587

<212> TYPE: PRT
<213> ORGANISM: Minute Virus of Mice

<400> SEQUENCE: 7

```
Met Ser Asp Gly Thr Ser Gln Pro Asp Ser Gly Asn Ala Val His Ser
1               5                   10                  15

Ala Ala Arg Val Glu Arg Ala Ala Asp Gly Pro Gly Ser Gly Gly Gly
            20                  25                  30

Gly Gly Ser Gly Gly Gly Val Gly Val Ser Thr Gly Ser Tyr Asp
            35                  40                  45

Asn Gln Thr His Tyr Arg Phe Leu Gly Asp Gly Trp Val Glu Ile Thr
    50                  55                  60

Ala Leu Ala Thr Arg Leu Val His Leu Asn Met Pro Lys Ser Glu Asn
65                  70                  75                  80

Tyr Cys Arg Ile Arg Val His Asn Thr Thr Asp Thr Ser Val Lys Gly
                85                  90                  95

Asn Met Ala Lys Asp Asp Ala His Glu Gln Ile Trp Thr Pro Trp Ser
            100                 105                 110

Leu Val Asp Ala Asn Ala Trp Gly Val Trp Leu Gln Pro Ser Asp Trp
            115                 120                 125

Gln Tyr Ile Cys Asn Thr Met Ser Gln Leu Asn Leu Val Ser Leu Asp
    130                 135                 140

Gln Glu Ile Phe Asn Val Val Leu Lys Thr Val Thr Glu Gln Asp Leu
145                 150                 155                 160

Gly Gly Gln Ala Ile Lys Ile Tyr Asn Asn Asp Leu Thr Ala Cys Met
                165                 170                 175

Met Val Ala Val Asp Ser Asn Asn Ile Leu Pro Tyr Thr Pro Ala Ala
            180                 185                 190

Asn Ser Met Glu Thr Leu Gly Phe Tyr Pro Trp Lys Pro Thr Ile Ala
            195                 200                 205

Ser Pro Tyr Arg Tyr Tyr Phe Cys Val Asp Arg Asp Leu Ser Val Thr
    210                 215                 220

Tyr Glu Asn Gln Glu Gly Thr Val Glu His Asn Val Met Gly Thr Pro
225                 230                 235                 240

Lys Gly Met Asn Ser Gln Phe Phe Thr Ile Glu Asn Thr Gln Gln Ile
                245                 250                 255

Thr Leu Leu Arg Thr Gly Asp Glu Phe Ala Thr Gly Thr Tyr Tyr Phe
            260                 265                 270

Asp Thr Asn Ser Val Lys Leu Thr His Thr Trp Gln Thr Asn Arg Gln
            275                 280                 285

Leu Gly Gln Pro Pro Leu Leu Ser Thr Phe Pro Glu Ala Asp Thr Asp
    290                 295                 300

Ala Gly Thr Leu Thr Ala Gln Gly Ser Arg His Gly Thr Thr Gln Met
305                 310                 315                 320

Gly Val Asn Trp Val Ser Glu Ala Ile Arg Thr Arg Pro Ala Gln Val
                325                 330                 335

Gly Phe Cys Gln Pro His Asn Asp Phe Glu Ala Ser Arg Ala Gly Pro
            340                 345                 350

Phe Ala Ala Pro Lys Val Pro Ala Asp Ile Thr Gln Gly Val Asp Lys
            355                 360                 365

Glu Ala Asn Gly Ser Val Arg Tyr Ser Tyr Gly Lys Gln His Gly Glu
    370                 375                 380

Asn Trp Ala Ser His Gly Pro Ala Pro Glu Arg Tyr Thr Trp Asp Glu
385                 390                 395                 400
```

Thr Ser Phe Gly Ser Gly Arg Asp Thr Lys Asp Gly Phe Ile Gln Ser
                405                 410                 415

Ala Pro Leu Val Val Pro Pro Leu Asn Gly Ile Leu Thr Asn Ala
            420                 425                 430

Asn Pro Ile Gly Thr Lys Asn Asp Ile His Phe Ser Asn Val Phe Asn
            435                 440                 445

Ser Tyr Gly Pro Leu Thr Ala Phe Ser His Pro Ser Pro Val Tyr Pro
450                 455                 460

Gln Gly Gln Ile Trp Asp Lys Glu Leu Asp Leu Glu His Lys Pro Arg
465                 470                 475                 480

Leu His Ile Thr Ala Pro Phe Val Cys Lys Asn Asn Ala Pro Gly Gln
                485                 490                 495

Met Leu Val Arg Leu Gly Pro Asn Leu Thr Asp Gln Tyr Asp Pro Asn
            500                 505                 510

Gly Ala Thr Leu Ser Arg Ile Val Thr Tyr Gly Thr Phe Phe Trp Lys
            515                 520                 525

Gly Lys Leu Thr Met Arg Ala Lys Leu Arg Ala Asn Thr Thr Trp Asn
530                 535                 540

Pro Val Tyr Gln Val Ser Ala Glu Asp Asn Gly Asn Ser Tyr Met Ser
545                 550                 555                 560

Val Thr Lys Trp Leu Pro Thr Ala Thr Gly Asn Met Gln Ser Val Pro
                565                 570                 575

Leu Ile Thr Arg Pro Val Ala Arg Asn Thr Tyr
            580                 585

<210> SEQ ID NO 8
<211> LENGTH: 1794
<212> TYPE: DNA
<213> ORGANISM: Artificial Sequence
<220> FEATURE:
<223> OTHER INFORMATION: modified from Minute Virus of Mice

<400> SEQUENCE: 8
atgggatgga gccaccccca gttcgagaag ggatctgatg gcacttcaca accggattct      60
ggaaacgctg ttcactcggc tgctagggtg gaaagggctg ctgatggacc tggcggatcc     120
ggtggaggag ttctggtgg aggtggagtc ggagtttcca ctggttctta cgacaaccag     180
acacactacc gtttcctggg cgatggatgg tcgagatca ccgctctcgc cactcgcttg     240
gttcacctga acatgcctaa gtcggaaaac tactgccgta tccgcgttca acaccact      300 gacacctctg tgaagggtaa catggctaag gacgatgccc acgagcaaat ctggactcct     360
tggagcttgg tggacgctaa cgcctggggc gtttggctgc agccatcaga ttggcaatac     420
atctgtaaca ccatgtcgca gctcaacttg gtctccctgg accaagaaat cttcaacgtg     480
gtcctcaaga ccgtgactga acaggacttg ggaggtcaag ctatcaagat tacaacaac      540 gacctcaccg cttgcatgat ggtggccgtc gattctaaca acatcttgcc ttacacccca     600
gctgccaaca gcatggagac tctgggtttc tacccgtgga agcccaccat cgcctcacct     660
taccgttact acttctgtgt tgaccgcgat ctgtcggtga cctacgagaa ccaggaaggc     720
actgtggaac acaacgtcat gggcacccca aagggaatga actcccaatt cttcacaatc     780
gagaacaccc agcaaatcac tctgctcagg acaggcgacg agttcgctac aggaacctac     840
tacttcgata ctaacagcgt gaagctcact cacacatggc agacaaacag acagttgggt     900 caacccctt tgctgtcaac attccctgag gctgacaccg atgccggcac cctgactgct     960

```
cagggttcca ggcacggcac aacccaaatg ggagttaact gggtgtctga ggctatcagg    1020
accagaccgg cccaagtggg attctgccaa ccccacaacg acttcgaggc ttcccgtgct    1080
ggtccattcg ctgctcctaa ggtcccagct gacatcactc agggagttga taaggaggcc    1140
aacggttcag tgcgctactc gtacggaaag caacacggtg aaaactgggc tagccacggc    1200
cctgctccag agaggtacac ctgggacgaa actagcttcg gttcaggcag agacaccaag    1260
gatggattca tccagtctgc tccgctggtt gtgccaccgc ccctgaacgg tatcctcaca    1320
aacgccaacc ctatcggcac caagaacgac atccacttca gcaacgtctt caactcatac    1380
ggtccactga ccgctttctc gcacccatcc ccagtgtacc cacagggaca aatctgggac    1440
aaggagctgg atctcgaaca aagcctcgc ctccacatca ctgctccatt cgtctgtaag    1500
aacaacgctc caggacagat gctcgtgagg ttgggaccta acctgacaga ccaatacgat    1560
ccaaacggcg ctaccctctc cagaatcgtc acttacggta cattcttctg gaagggcaag    1620
ttgaccatgc gtgctaagct gcgcgccaac actacatgga acccagtcta ccaggtttcc    1680
gccgaggaca acggaaactc ttacatgagc gtgactaagt ggctccccac agctaccggt    1740
aacatgcaat ctgtgccgtt gatcactagg cccgtcgcca gaaacacata ctaa          1794
```

<210> SEQ ID NO 9
<211> LENGTH: 597
<212> TYPE: PRT
<213> ORGANISM: Artificial Sequence
<220> FEATURE:
<223> OTHER INFORMATION: Modified from Minute Virus of Mice

<400> SEQUENCE: 9

```
Met Gly Trp Ser His Pro Gln Phe Glu Lys Gly Ser Asp Gly Thr Ser
1               5                   10                  15

Gln Pro Asp Ser Gly Asn Ala Val His Ser Ala Ala Arg Val Glu Arg
            20                  25                  30

Ala Ala Asp Gly Pro Gly Gly Ser Gly Gly Gly Ser Gly Gly Gly
        35                  40                  45

Gly Val Gly Val Ser Thr Gly Ser Tyr Asp Asn Gln Thr His Tyr Arg
    50                  55                  60

Phe Leu Gly Asp Gly Trp Val Glu Ile Thr Ala Leu Ala Thr Arg Leu
65                  70                  75                  80

Val His Leu Asn Met Pro Lys Ser Glu Asn Tyr Cys Arg Ile Arg Val
                85                  90                  95

His Asn Thr Thr Asp Thr Ser Val Lys Gly Asn Met Ala Lys Asp Asp
            100                 105                 110

Ala His Glu Gln Ile Trp Thr Pro Trp Ser Leu Val Asp Ala Asn Ala
        115                 120                 125

Trp Gly Val Trp Leu Gln Pro Ser Asp Trp Gln Tyr Ile Cys Asn Thr
    130                 135                 140

Met Ser Gln Leu Asn Leu Val Ser Leu Asp Gln Glu Ile Phe Asn Val
145                 150                 155                 160

Val Leu Lys Thr Val Thr Glu Gln Asp Leu Gly Gly Gln Ala Ile Lys
                165                 170                 175

Ile Tyr Asn Asn Asp Leu Thr Ala Cys Met Met Val Ala Val Asp Ser
            180                 185                 190

Asn Asn Ile Leu Pro Tyr Thr Pro Ala Ala Asn Ser Met Glu Thr Leu
        195                 200                 205

Gly Phe Tyr Pro Trp Lys Pro Thr Ile Ala Ser Pro Tyr Arg Tyr Tyr
    210                 215                 220
```

```
Phe Cys Val Asp Arg Asp Leu Ser Val Thr Tyr Glu Asn Gln Glu Gly
225                 230                 235                 240

Thr Val Glu His Asn Val Met Gly Thr Pro Lys Gly Met Asn Ser Gln
            245                 250                 255

Phe Phe Thr Ile Glu Asn Thr Gln Gln Ile Thr Leu Leu Arg Thr Gly
        260                 265                 270

Asp Glu Phe Ala Thr Gly Thr Tyr Tyr Phe Asp Thr Asn Ser Val Lys
    275                 280                 285

Leu Thr His Thr Trp Gln Thr Asn Arg Gln Leu Gly Gln Pro Pro Leu
290                 295                 300

Leu Ser Thr Phe Pro Glu Ala Asp Thr Asp Ala Gly Thr Leu Thr Ala
305                 310                 315                 320

Gln Gly Ser Arg His Gly Thr Thr Gln Met Gly Val Asn Trp Val Ser
            325                 330                 335

Glu Ala Ile Arg Thr Arg Pro Ala Gln Val Gly Phe Cys Gln Pro His
        340                 345                 350

Asn Asp Phe Glu Ala Ser Arg Ala Gly Pro Phe Ala Ala Pro Lys Val
    355                 360                 365

Pro Ala Asp Ile Thr Gln Gly Val Asp Lys Glu Ala Asn Gly Ser Val
370                 375                 380

Arg Tyr Ser Tyr Gly Lys Gln His Gly Glu Asn Trp Ala Ser His Gly
385                 390                 395                 400

Pro Ala Pro Glu Arg Tyr Thr Trp Asp Glu Thr Ser Phe Gly Ser Gly
            405                 410                 415

Arg Asp Thr Lys Asp Gly Phe Ile Gln Ser Ala Pro Leu Val Val Pro
        420                 425                 430

Pro Pro Leu Asn Gly Ile Leu Thr Asn Ala Asn Pro Ile Gly Thr Lys
    435                 440                 445

Asn Asp Ile His Phe Ser Asn Val Phe Asn Ser Tyr Gly Pro Leu Thr
450                 455                 460

Ala Phe Ser His Pro Ser Pro Val Tyr Pro Gln Gly Gln Ile Trp Asp
465                 470                 475                 480

Lys Glu Leu Asp Leu Glu His Lys Pro Arg Leu His Ile Thr Ala Pro
            485                 490                 495

Phe Val Cys Lys Asn Asn Ala Pro Gly Gln Met Leu Val Arg Leu Gly
        500                 505                 510

Pro Asn Leu Thr Asp Gln Tyr Asp Pro Asn Gly Ala Thr Leu Ser Arg
    515                 520                 525

Ile Val Thr Tyr Gly Thr Phe Phe Trp Lys Gly Lys Leu Thr Met Arg
530                 535                 540

Ala Lys Leu Arg Ala Asn Thr Thr Trp Asn Pro Val Tyr Gln Val Ser
545                 550                 555                 560

Ala Glu Asp Asn Gly Asn Ser Tyr Met Ser Val Thr Lys Trp Leu Pro
            565                 570                 575

Thr Ala Thr Gly Asn Met Gln Ser Val Pro Leu Ile Thr Arg Pro Val
        580                 585                 590

Ala Arg Asn Thr Tyr
        595

<210> SEQ ID NO 10
<211> LENGTH: 1611
<212> TYPE: DNA
<213> ORGANISM: Xenotropic Murine Leukemia Virus
```

```
<400> SEQUENCE: 10
atgggacaga ccgtaaccac tcctttgagt ctgaccctag aacactgggg agacgtccag      60
cgcattgcgt ccaaccagtc cgtggacgtc aagaagagac gttgggtcac cttctgctct     120
gccgagtggc caactttcga tgtggggtgg ccgcaagatg gtacttttaa tttggacatt     180
attttacagg ttaaatctaa ggtgttctct cccggtcccc acggacaccc ggatcaggtc     240
ccatacattg tcacctggga ggcacttgcc tatgaccccc ctccgtgggt caaaccgttt     300
gtctctccaa accccctcc cttaccgaca gctcccgtcc tccgcccgg tccttctgcg       360 caacctccgt cccgatctgc cctttaccct gccttaccc cctctataaa gtccaaacct      420
cctaagcccc aggttctccc tgatagcggc ggacctctca ttgaccttct cacagaggac     480
cccccgccgt acgagcaca accttcctcc tctgccagag aaaacaatga agaagaggcg      540
gccgccacct ccgaggtttc cccccttct cccatggtgt ctcgactgcg gggaaggagg      600
gaccctcccg cagcggactc cacctcctcc caggcattcc cactccgcat ggggggagat     660
ggccagcttc agtattggcc gttttcctcc tcggacttat acaattggaa aaataataac     720
ccttcctttt ctgaagaccc aggtaaattg acggccttga ttgagtccgt cctcatcacc     780
caccagccca cctgggacga ctgtcagcag ttgttaggga ccctgctgac cggagaagaa     840
aagcagcggg tgctcctaga ggctagaaag gcagtccggg gcaatgatgg acgcccccact    900 cagttgccta atgaagtcaa tgctgctttt ccccttgaac gccccgattg ggattacacc     960
actacagaag gtaggaacca cctagtcctc tatcgccagt tgctcttagc gggtctccaa    1020
aacgcgggca gaagccccac caatttggcc aaggtaaaag ggataaccca gggacctaat    1080
gagtctccct cagccttttt agagagactc aaggaggcct atcgcaggta cactccttat    1140
gaccctgagg acccagggca agaaaccaat gtgtctatgt cattcatctg gcagtctgcc    1200
ccggatatcg ggcgaaagtt agagcggtta gaagatttaa agagcaagac cttaggagat    1260
ttagtgaggg aagctgaaaa gatctttaat aagcgagaaa ccccggaaga agagaggaa     1320 cgtatcagga gagaaacaga ggaaaaagaa gaacgccgta gggcagagga tgagcagaga    1380
gagaaagaaa gggaccgcag aagacataga gagatgagca agctcttggc cactgtagtt    1440
attggtcaga gacaggatag acagggggga gagcggagga ggccccaact tgataaggac    1500
caatgcgcct actgcaaaga aaagggacac tgggctaagg actgcccaaa gaagccacga    1560
gggccccgag gaccgaggcc ccagacctcc ctcctgacct taggtgacta g             1611

<210> SEQ ID NO 11
<211> LENGTH: 1935
<212> TYPE: DNA
<213> ORGANISM: Xenotropic Murine leukemia Virus

<400> SEQUENCE: 11
atggaaggtt cagcgttctc aaaacccctt aaagataaga ttaacccgtg gggccccta      60 atagttatgg ggatcttggt gagggcagga gcctcggtac aacgtgacag ccctcaccag    120
atcttcaatg ttacttggag agttaccaac ctaatgacag acaaacagc taacgccacc     180 tccctcctgg ggacgatgac agacaccttc cctaaactat attttgacct gtgtgattta    240
gtaggagact actgggatga cccagaaccc gatattgggg atggttgccg cactcccggg    300
ggaagaagaa ggacaagact gtatgacttc tatgtttgcc ccggtcatac tgtaccaata    360
gggtgtggag gccggggaga gggctactgt ggcaaatggg gatgtgagac cactggacag    420
gcatactgga agccatcatc atcatgggac ctaatttccc ttaagcgagg aaacactcct    480
```

```
aaggatcagg gcccctgtta tgattcctcg gtctccagtg gcgtccaggg tgccacaccg      540
gggggtcgat gcaacccct  ggtcttagaa ttcactgacg cgggtagaaa ggccagctgg      600 gatgcccca  aagtttgggg actaagactc tatcgatcca caggggccga cccggtgacc      660
cggttctctt tgacccgcca ggtcctcaat gtaggacccc gcgtccccat tgggcctaat      720
cccgtgatca ctgaccagct accccatcc  caacccgtgc agatcatgct ccccaggcct      780
cctcatcctc ctccttcagg cacggtctct atggtacctg gggctccccc gccttctcaa      840
caacctggga cgggagacag gctgctaaat ctggtagaag gagcctacca agcactcaac      900
ctcaccagtc ctgacaaaac ccaagagtgc tggttgtgtc tggtatcggg accccctac       960 tacgaagggg ttgccgtcct aggtacctac tccaaccata cctctgcccc agctaactgc     1020
tccgtggcct cccaacacaa gctgaccctg tccgaagtaa ccggacaggg actctgcgta     1080
ggagcagttc ccaaaaccca tcaggccctg tgtaatacca cccagaagac gagcgacggg     1140
tcctactatc tggctgctcc cgccgggacc atctgggctt gcaacaccgg gctcactccc     1200
tgcctatcta ctactgtact caacctcacc accgattact gtgtcctggt tgagctctgg     1260
ccaaaggtaa cctaccactc ccctgattat gtttatggcc agtttgaaaa gaaaactaaa     1320
tataaaagag agccggtgtc attaactctg gccctgctgt tgggaggact tactatgggc     1380
ggcatagctg caggagtagg aacagggact acagccctag tggccaccaa acaattcgag     1440
caactccagg cagccataca tacagacctt ggggccttag aaaaatcagt cagtgcccta     1500
gaaaagtctc tgacctcgtt gtctgaggtg gtcctacaga accggagagg attagatctg     1560
ctgttcctaa aagaaggagg attatgtgct gccctaaaag aagaatgctg tttctacgcg     1620
gaccacactg gcgtagtaag ggatagcatg gctaagctaa gagagagact aaaccagaga     1680
caaaaattgt tcgaatcagg acaagggtgg tttgagggac tgtttaacag gtccccatgg     1740
ttcacgaccc tgatatccac cattatgggc cctctgatag tacttttatt aatcctactc     1800
ctcggaccct gcattctcaa ccgcttggtc cagtttgtaa aagacagaat ttcagtagta     1860
caggccctga ttctgaccca acagtatcac caactcaaat caatagaacc agaagaagta     1920
gaatcgcgtg aataa                                                      1935
```

METHODS AND KITS FOR QUANTIFYING THE REMOVAL OF MOCK VIRUS PARTICLES FROM A PURIFIED SOLUTION

SUMMARY OF THE INVENTION

The present invention relates to a method of quantifying the amount of Mock Virus Particles (MVP) removed from a solution as a result of processing that solution through a purification technique. This method involves the steps of adding MVP to a solution, processing the solution through a purification technique, and then quantifying the amount of MVP removed from the solution. The present invention also relates to a kit that can be used in conjunction with the method. This kit preferably will comprise at least one stock solution of MVP and at least one quantification solution.

BACKGROUND

Biopharmaceutical products, such as monoclonal antibodies, recombinant proteins, vaccines, blood derivatives and animal products carry a risk of transmitting infectious viruses (Burnouf, 2005; Aranha, 2011). This is due to either endogenous virus being present in the source material used for biopharmaceutical manufacturing or the risk of exogenous "adventitious" virus contaminating a biopharmaceutical containing solution during manufacturing (Kerr, 2010). As a result, manufacturers of biopharmaceutical products are required by international regulatory agencies to incorporate sufficient virus clearance steps into their manufacturing processes and to validate these steps by providing robust viral clearance data (EMEA, 2008; EMEA, 2008; ICH, 1997; ICH, 998; FDA, 1997).

To validate viral clearance, viral "spiking studies" are performed whereby live virus is added to biopharmaceutical material and scaled down purification process steps are performed (Darling, 2002). The step's ability to reduce virus is then analyzed by quantifying the remaining virus in solution via infectivity assay ($TCID_{50}$) or quantitative polymerase chain reaction techniques (Q-PCR). These studies are usually conducted by third party contract labs due to the expertise and additional safety measures required to propagate and quantify live viral particles. As a result these studies are extremely expensive and logistically difficult to conduct. In effect, process steps are typically developed for months or years before they are evaluated for virus removal efficacy. This practice increases regulatory risk as time and money are spent developing process steps that may ultimately fail to sufficiently remove virus during regulatory enabling validation studies. Thus, there is a need for new and improved methods of determining virus removal efficiency during purification processes development.

SUMMARY OF THE INVENTION

The present invention relates to a method of quantifying the amount of Mock Virus Particle (MVP) removed from a solution as a result of processing the solution through a purification technique. The steps of the method include; adding MVP to a solution, processing the solution through a purification technique, and quantifying the amount of MVP removed from the solution. In a preferred embodiment, the solution to which MVP is added contains a biologic of interest. In an even more preferred embodiment, the biologic of interest is an antibody, non-antibody protein, vaccine, nucleic acid product, blood or plasma derivative. In another even more preferred embodiment, the biologic of interest is produced by a cell culture process or a fermentation process which utilizes human cells, animal cells, plant cells, insect cells, hybridoma cells, yeast cells, or bacteria cells. In another even more preferred embodiment, a biologic of interest present in the solution is purified by way of processing of that solution through the purification technique.

In another preferred embodiment, the purification technique that processes a solution containing MVP is a chromatography, filtration, ultrafiltration, centrifugation, or viral inactivation technique. In another preferred embodiment, the quantity of MVP added to a solution prior to processing that solution through a purification technique is greater than the quantity of MVP in solution remaining after processing.

In a preferred embodiment, MVP comprises viral capsid protein, viral envelope protein, or both a viral capsid and a viral envelope protein. In an even more preferred embodiment, the viral capsid or envelope protein is produced by a bacteria, yeast, plant, insect, and/or animal and/or human cell. In another even more preferred embodiment the viral capsid or envelope protein is derived from a Parvoviridae or Retroviridae source. In another even more preferred embodiment, the viral capsid or envelope protein comprises a heterologous epitope. In another even more preferred embodiment, MVP contains in vitro nucleic acid.

In a preferred embodiment, quantifying the amount of MVP removed from the solution comprises the use of a quantification technique for determining the amount of MVP in a solution including Enzyme Linked Immunosorbent Assay (ELISA), Polymerase Chain Reaction (PCR), nano-imaging, fluorescence, enzymatic, microscopy, spectrophotometry, Transmission Electron Microscopy (TEM), or western blot techniques. In an even more preferred embodiment, the quantification technique uses an antibody capable of binding to a capsid protein epitope, an envelope protein epitope, or a heterologous epitope present on the surface of the MVP. In another even more preferred embodiment, the quantification technique uses an antibody capable of binding to a linker molecule that is bound to the MVP. In another even more preferred embodiment, the quantification technique uses a molecule bound to the MVP and an antibody capable of binding to the molecule or a primer capable of binding to a nucleic acid segment that is attached to the molecule. In another even more preferred embodiment, the quantification technique uses a primer capable of binding to an in vitro nucleic acid sequence contained within the MW.

The present invention relates to a method whereby MVP is added to a solution, the solution is processed through a purification technique, and the amount of MVP removed from solution is quantified In a preferred embodiment, a second species of MVP is added to the solution, the solution is processed through a purification technique, and the amount of the second species of MVP removed from solution is quantified In an even more preferred embodiment, the first and second species of MVP are added to a solution at the same time or sequentially. In another even more preferred embodiment, two or more additional species of MVP are added to the solution.

The present invention also relates to a kit which comprises: at least one container comprising a stock solution of MVP, and at least one container comprising a quantification solution. In a preferred embodiment, the quantification solution comprises an antibody capable of binding to MVP or to a molecule which can be bound to MVP. In an even more preferred embodiment, the kit further comprises a solution of a second antibody, capable of binding to the antibody which is capable of binding to MVP or to a molecule which can be bound to MVP. In another even more preferred embodiment, the antibody capable of binding to MVP is conjugated to an enzyme. In another even more preferred embodiment, the second antibody capable of binding to the antibody which is capable of binding to MVP or a molecule which can bind to MVP is conjugated to an enzyme. In another preferred embodiment, the kit further contains an ELISA plate containing an immobilized antibody or molecule that can bind to MVP. In another preferred embodiment, the quantification solution comprises primers capable of binding to an in vitro nucleic acid sequence or a segment of nucleic acid bound to a molecule which can be bound to MVP. In another preferred embodiment, the kit contains another container comprising a solution of a molecule which can bind to MVP. In another preferred embodiment, the kit also contains additional reagents for performing ELISA or PCR techniques.

BRIEF DESCRIPTION OF THE DRAWINGS

Embodiments are illustrated by way of example and not limitation in the figures of the accompanying drawings, in which like references indicate similar elements and in which:

Mouse Minute Virus (MMV) MVP's were purified via methods referred to in Examples 1 and 2. To determine the purity of the Cesium Chloride density gradient fractions, samples from each density fraction (lanes 1-13) were reduced and electrophoresed on a 4-12% polyacrylamide gel. Protein bands were visualized through Commassie blue staining. A VP2 protein standard (alpha diagnostic cat #MVMVP25-R-10) was run in lane "S" for comparison (VP2 protein is expected to be 64 KDa) and a molecular weight marker protein was run in lane "M". In FIG. 1, MVP resulting from natural VP2 protein formation was analyzed. Fractions 11-13 were pooled to form MVP stock solution. Based on staining results, the pooled stock solution contained MVP at a purity of >95%. In FIG. 3, MVP resulting from recombinant VP2 protein formation was analyzed. Fractions 11-13 were pooled to form MVP stock solution. Based on staining results, the pooled stock solution contained MVP at a purity of ~90%.

MMV MVP stock solutions were produced via methods described in Examples 1 and 2. In FIG. 2, TEM images were taken of MMV MVP stock solution resulting from the assembly of 60 copies of natural (non-modified) VP2 protein. In FIG. 4, TEM images were taken of MMV MVP stock solution resulting from the assembly of 60 copies of recombinant VP2 proteins, each containing a heterologous epitope (strep II tag amino acid sequence). Images were captured after negative staining Two microliters of each stock solution were placed onto separate formvar/carbon-coated electron microscope grids and allowed to air dry. After ten minutes, residual material was wicked from the grids. The grids were then fixed and stained by placing 20 microliters of 2.0% phosphotungstic acid (PTA), pH 7.0, onto each grid for one minute. The excess PTA was then removed, and the grids were examined, quantified and photographed using an FEI Tecnai Spirit Twin microscope at a magnification of 165,000×. Results show concentrations of $3.06 \times 10^{13}$ MMV MVP/ml of stock solution (FIG. 2) and $3.56 \times 10^{13}$ heterologous epitope MMV MVP/ml of stock solution (FIG. 4).

DETAILED DESCRIPTION OF INVENTION

Figure 1:
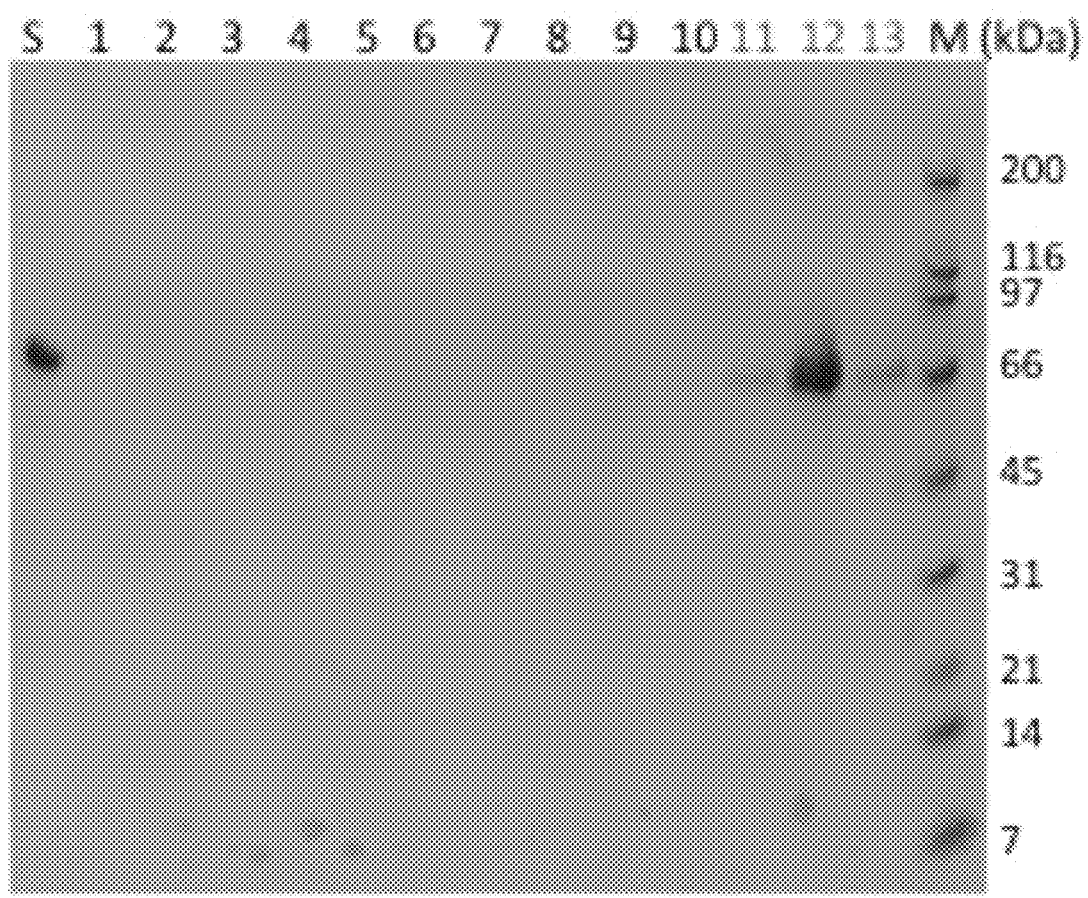
FIG. 1: Purity of MMV MVP fractions

In the present invention, the term "mock virus particle (MVP)" refers to a non-infectious, non-replicating assembled unit comprised of synthetically produced (e.g. recombinantly expressed or chemically synthesized) viral capsid protein, viral envelope protein, or viral capsid and envelope proteins. MVP's do not refer to virus particles found in nature, including, but not limited to live virus particles, virus particles found in nature that have naturally lost the ability to be infectious, or virus particles that have lost the ability to be infectious in vitro, such as "ultraviolet irradiated", "heat-killed" or "heat-inactivated" viral particles. Thus, the synthetic nature of a MVP provides their ability to be easily produced and used in a commercial setting as compared to other forms of virus particles used in the art. The term "viral capsid protein" refers to a protein of any virus that comprises a shell around its genome. The term "viral envelope protein" refers to any viral protein that covers a capsid protein shell and becomes part of the outer layer of a virus. Certain viral capsid and envelope proteins are known to be prevalent to viruses within specific viral taxonomic families. MVPs can be produced from the capsid or envelope proteins of these viral families resulting in units that physiochemically resemble specific viruses from within those families. However, assembled units of MVP lack genetic similarity to these viruses (MVP's may not contain any nucleic acid whatsoever). Examples of major viral capsid and envelope proteins (common names of these proteins referred to in the art) and their associated viral family are listed in Table 1 below along with an example MVP which could assemble from one or more of those proteins (Fauquet et. al, 2005).

TABLE 1

| Virus Family | Known Capsid Protein Examples | Known Envelope Protein Examples | Example MVP |
|---|---|---|---|
| Parvoviridae | VP1, VP2, VP3, VP4 | None | Mouse Minute Virus - MVP |
| Retroviridae | MA, CA, NC (gag proteins) | SU, TM, LP (env proteins), Sag | Xenotropic Murine Leukemia Virus- |
| Reoviridae | μ1, μ2, μA, μB, λ1, λ2, λ3, λA, λB, λC, σ1, σ2, σ3, σA, σB, σC, VP1, VP2, VP3, VP4, VP5, VP6, VP7, CSP, LPP, TP, P1, P2, P3, P5, P7, P8 | None | Reovirus Type 3 - MVP |
| Caliciviridae | VP60, VP62, VP8.5, VP10, CP | None | Feline Calicivirus - MVP |

TABLE 1-continued

| Virus Family | Known Capsid Protein Examples | Known Envelope Protein Examples | Example MVP |
|---|---|---|---|
| Tymoviridae | CP | None | *Physalis* mottle-MVP |
| Herpesviridae | VP5, VP1-3, VP23, VP26 VP19C, VP21, VP24, VP22, UL16, MCP, CP62, U56, U29, U57 | gM, gB, gD, gL, gH, gC, gE, gO, gI, gG gK, gJ, gN, BMRF2, BDFL2, UL45H, UL34, US9 | Herpes simplex - MVP |
| Togaviridae | CP | E1, E2, E3 | Rubella -MVP |
| Coronaviridae | N | S, M, E, HE | Infectious bronchitis - MVP |
| Orthomyxoviridae | NP, PA, $PB_1$, $PB_2$ | HA, NA, $M_1$, $M_2$, HEF, GP, NB, $BM_2$, $CM_2$ | Influenza A - MVP |
| Filoviridae | NP, VP30, VP35, L | GP, VP24, VP40 | Ebola - MVP |
| Hepadnaviridae | HBc | L, M, S | Hepatitis B - MVP |
| Paramyxoviridae | NP, P | M, F, HN, SH, G, H | Human Parainfluenza 3-MVP |
| Flaviviridae | C | M, E, prM, $E^{ms}$, E1, E2 | Bovine Viral Diarrhea-MVP |
| Picornavirus | VP1, VP2, VP3, VP4, Vpg, VP0 | None | Hepatitis A-MVP |
| Polyomaviridae | Vp1, Vp2, Vp3 | None | Simian Virus 40 - MVP |

In the present invention, a MVP unit assembles as the result of recombinantly expressing or chemically synthesizing viral capsid or viral envelope proteins in vitro. Preferably, viral capsid and envelope proteins which assemble to form a MVP are expression products from naturally occurring viral protein nucleic acids sequences. Alternatively, they are expression products from viral protein nucleic acid sequences that have been altered, or modified, in vitro. In the present invention, protein products which are composed of altered or modified amino acid sequences as a result of the expression of altered or modified nucleic acid sequences are referred to as "recombinant" proteins. The act of altering or modifying naturally occurring viral protein nucleic acid sequences to express recombinant viral capsid or envelope proteins is well known in the art (see, for example, Gillock, 1998). Preferably, recombinant MVP capsid or envelope proteins are 99.9% or more homologous to their natural viral protein sources, according to standard protein based BLAST homology searches. Alternatively, recombinant capsid or envelope proteins of MVP are at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% homologous to their natural capsid and/or envelope protein sources, according to standard BLAST homology searches.

Preferably, viral capsid or envelope proteins which assemble to form MVPs are produced by expressing their genes in bacteria, yeast, plant, insect, animal, or human cells. The act of producing these proteins in lieu of assembling a MVP is commonly known in the art (see for example, Makarova 2011). For example, natural or modified viral nucleic acid protein sequences are first cloned into expression vectors. Preferably, expression vectors are yeast based expression vectors, bacterial based expression vectors, baculovirus based expression vectors, and/or mammalian based expression vectors, and/or plant-based expression vectors. The expression vector is then made to transfect a cell. Preferably, cells that may be transfected include, but are not limited to; bacteria, yeast, plant, insect, animal, mammal and/or human cells. Preferably, after the expression of natural or recombinant viral capsid or envelope proteins, the proteins spontaneously assemble into MVP. Alternatively, the assembly of MVP will not occur spontaneously. In these instances, the un-assembled protein containing solution could be treated with chemicals and/or proteins to increase the occurrence of MVP assembly. Alternatively, the un-assembled protein containing solution will be purified to increase the amount of capsid and or envelope proteins in solution relative to other molecules in solution.

Preferably, the nucleic acid sequence expressed to produce a viral capsid or envelope protein which assembles to form a MVP is derived from a Parvoviridae or Retroviridae genomic source. Examples of Parvoviridae derived nucleic acid sequence sources include, but are not limited to the genomes of, Minute Virus of Mice (Mouse Minute Virus), Canine Parvovirus, Feline Parvovirus, Porcine Parvovirus, B19 virus, Adeno-associated virus 1, Junonia coenia densovirus, Bombyx mori virus, and Aedes aegypti densovirus genomes. Examples of viral capsid proteins which could be produced and assembled to form MVP from these genomes include, but are not limited to, VP1, VP2, VP3, or VP4 proteins. Examples of Retroviridae derived nucleic acid protein sequence sources include, but are not limited to the genomes of, Avian Erythroblastosis Virus, Avian Leukosis Virus, Avian Myeloblastosis Virus, Avian Sarcoma Virus, Avian Myelocytomatosis Virus, Esh Sarcoma Virus, Fujinami Sarcoma Virus, Golden Pheasant Virus, Induced Leukemia Virus, Lymphoid Leukosis Virus, Myeloblastosis-associated Virus, Myelocytomatosis Virus, Rous-associated Virus, Ring-necked Pheasant Virus, Rous Sarcoma Virus, NK-24, SKV, Baboon Endogenous Virus, BEV, CCC, CERV-CI, CPC4, Corn Snake Retrovirus, Chicken Syncytial Virus, Duck Infectious Anemia Virus, Deer Kidney Virus, DPC4, Equine Dermal Fibrosarcoma Virus, Feline Leukemia Virus, FeLV-AIDS, Feline Sarcoma Virus, Fr-MLV, Fr-SFFV, FS-1, Gibbon Ape Leukemia Virus, Hamster Leukemia Virus, Lymphoproliferative Disease Virus, Mink Cell Focus-inducing Virus, MAIDS, MDEV, Mink Leukemia Virus, Murine Leukemia Virus, MMCA, Murine Sarcoma Virus, Myeloid Leukemia Virus, OMCA, PK-1S, R-35, RadLV, Rat Leukemia Virus, Ra-MCF, Ra-MLV, Ra-SFFV, Rat Sarcoma Virus, RDL14, Reticuloendotheliosis-associated Virus, Spleen Focus-forming Virus, Simian Sarcoma Virus, Simian Lymphoma Virus, Simian Myelogenous Leukemia Virus, Spleen Necrosis Virus, Simian Sarcoma-associated Virus, Simian Sarcoma Virus, TRV4, Vand C-I, Viper Retrovirus, Woolly Monkey Virus, Woolly Monkey Leukemia Virus, Bovine Leukemia Virus, BoLV, Human T-cell Leukemia Virus, Simian T-cell Leukemia Virus, STLVpan-p, Bovine Syncytial Virus, Feline Syncytium-forming Virus, Human Foamy Virus, Simian Foamy Virus, Bovine Immunodeficiency Virus, Caprine Encephalitis-arthritis Virus, Equine Infectious Anemia Virus, Feline Immunodeficiency Virus, Goat Leukoencephalitis Virus, Human Immunodeficiency Virus, Jembrana, Maedi/visna Virus, Progressive Pneumonia Virus, Simian Immunodeficiency Virus, Mouse Mammary Tumor Virus, M432,M832, MNV, Mason-Pfizer Monkey Virus, PMFV, P0-1-Lu, Squirrel Monkey Retrovirus, Simian Retrovirus, Jaagsiekte Retrovirus, Walleye Dermal Sarcoma Virus, Walleye Dermal Hyperplasia Virus, and Gypsy genomes. Examples of viral capsid and envelope proteins which could be produced and assembled to form MVP from these Retroviridae genomes include, but are not limited to, gag proteins (MA, CA, NC), env proteins (SU, TM, LP), and Sag protein. Even more preferably, Retroviridae derived protein sources include genomic sequences from mammalian cell-endogenous retroviruses and retrovirus like particles. Examples of mammalian cell-endogenous retroviruses and retrovirus like particles include, but are not limited to Murine Leukemia Viruses (Ab, AKT8, Cas-Br-E, Du5H MAIDS, FMCF-98, Fr, Graffi, Gross, LP-BMS, Ki, Mo, MPLV, NT40, PVC-211, Ra, RadLV, SL3-3, TRI-3, XMuLV) and Intracisternal A type particles. Examples of mammalian cells that may contain endogenous retrovirus or retrovirus like particles include CHO, NS0, NS-1, Sp20Ag14, MH, BHK, and RH cells.

Preferably, a viral capsid or envelope protein assembles to form an MVP which displays an epitope(s) on its surface. In the present invention, an "epitope" is a specific sequence of amino acids displayed on the exterior surface of a MVP. Epitopes may be utilized to quantify the amount of MVP present in solution (and hence their removal from solution) without the need of infectivity assays, QPCR, or other cumbersome and expensive methods common to the art of quantifying infectious or non-infectious virus particle removal. In some instances, a recombinant viral capsid or envelope protein assembles to form an MVP. In these instances, the MVP may display a heterologous epitope(s) on its surface. In the present invention, a "heterologous epitope" refers to an epitope which results from the expression of recombinant capsid or envelope proteins. Likewise, an MVP can comprise a heterologous epitope when it is assembled from recombinant proteins. Examples of heterologous epitopes include but are not limited to, strep-tag (e.g. amino acid sequence WSHPQFEK (SEQ ID No:1)), flag tag (e.g. amino acid sequence DYKDDDDK (SEQ ID No:2)) and His-tag (e.g. amino acid sequence HHHHHH (SEQ ID No:3)). Preferably, one copy of an epitope or heterologous epitope may be present per protein unit of that MVP. Alternatively, multiple copies of an epitope or heterologous epitope may be present per protein unit of that MVP. Heterologous epitopes may enhance the sensitivity of quantification methods used to determine the amount of MVP in a solution to levels beyond what is achievable for infectivity assays, QPCR assays or other assays currently common in the art.

Preferably, a MVP does not contain any nucleic acid. Alternatively, a MVP may contain a segment of in vitro nucleic acid. In the present invention, a "segment of in vitro nucleic acid" refers to a specific sequence of nucleic acid that is purposefully introduced to an MVP solution as the particles are assembling so that the resulting MVP retains a copy of that sequence. Thus, unlike all other particles known to the art, MVP's do not rely on inherited genetic material of a viral genuine for quantifying their amount in solution. In the present invention, the term "inherited genetic material" refers to all naturally encapsulated nucleic acids present in a replicating or replication-deficient virus particle. For example, in the art the quantification of infectious virus particles involves either a measurement of infectivity (the result of naturally encapsulated genomic nucleic acid expression) or QPCR (utilizing primers against their naturally encapsulated genomic nucleic acid) (Shi, 2004). Likewise, in the art, the quantification of non-replicating endogenous retrovirus like particles involves QPCR utilizing primers against naturally encapsulated genomic nucleic acid or quantitative product enhanced reverse transcriptase (Q-PERT) which measures viral reverse transcriptase activity (Zhang, 2008). Preferably, a segment of in vitro nucleic acid may refer to a synthetically derived sequence of nucleic acid. Alternatively, a segment of in vitro nucleic acid may refer to a naturally derived sequence. Preferably, in the instance of a naturally derived sequence, the length of the sequence is about 1% or less, about 5% or less, about 10% or less, about 25%, about 30% or less, about 40% or less, about 50%, about 60% or less, about 70% or less, about 75% or less, about 90% or less, about 95% or less, or about 99% or less than the genome of the organism from which the sequence may have been derived, No amount of in vitro nucleic acid will be sufficient to allow for replication or infectivity of the MVP, as measured by methods common in the art, One example of a method commonly used in the art to measure infectivity is $TCID_{50}$. Unlike other virus particles common to the art, MVP's will thus have no risk of being or ever becoming infectious. In some instances, an in vitro nucleic acid segment may be derived from a viral source. In other instances, an in vitro nucleic acid may be derived from non-viral sources. Examples of in vitro nucleic acid sources include but are not limited to, virus, bacteria, yeast, insect, animal, and/or human. Preferably, in instances where in vitro nucleic acid is derived from viral sources, the viral source may be the same source from which the capsid or envelope proteins of the MVP were derived. Alternatively, in instances where in vitro nucleic acid is derived from viral sources, the viral source may be different from the source from which the capsid or envelope proteins of the MVP were derived. Even more preferably, in either case, the 5'-end and the 3'-end of the in vitro nucleic acid segment can contain unique sequences that are not present in the natural viral genome from which the sequence was derived.

Preferably, after assembly, the MVP may be purified using methods known in the art (Hernando, 2000), Moreover, the purity of MVP in its assembly solution after purification can be such that less than 65% of all proteins in solution are non-MVP related, less than 55% of all proteins in solution are non-MVP related, less than 45% of all proteins in solution are non-MVP related, less than 35% of all proteins in solution are non-MVP related, less than 25% of all proteins in solution are non-MVP related, less than 15% of all proteins in solution are non-MVP related, less than 5% of all proteins in solution are non-MVP related. In the present invention, the term "non-MVP related [proteins]" refers to all non-capsid and/or non-envelope proteins that do not assemble to form MVP. One example of a method to purify MVP is a sucrose density gradient. Another example is centrifugation. Another example is chromatography. The purity of MVP in a stock solution can be determined through methods common to the art including, but not limited to, Polyacrylamide Gel Electrophoresis (PAGE), high pressure liquid chromatography, mass spectroscopy, flow cytometry, ELISA, dynamic light scattering, gel filtration, or ultracentrifugation. In some instances, after assembly, MVP may be introduced to and reacted against a linker molecule so that the resulting MVP binds that linker molecule to its surface. In the present invention, the term "linker molecule" refers to a synthetic polymer or natural polymer (such as a protein) that can be covalently or bound to another molecule.

As previously described, MVP are assembled from viral capsid or envelope proteins. In the present invention, MVP are thus denoted according to their viral protein source. For example, MVP assembled from the VP2 protein (or recombinant versions of the MVP2 protein) of the Mouse Minute Virus would be referred to as an "MMV MVP". Another example would be referring to a MVP assembled from env and/or gag proteins (or recombinant versions of env and/or gag proteins) of the Xenotropic Murine Leukemia Virus (XMuLV) as "XMuLV MVP". In the present invention, MVP is preferably comprised of natural or recombinant viral proteins produced from Parvoviridae or Refroviridae nucleic acid sources. Alternatively, MVP is comprised of viral protein produced from nucleic acid sources of other virus families including, but not limited to, Caliciviridae, Reoviridae, Tymoviridae, Togaviridae, Herpesviridae, Coronaviridae, Orthomyxoviridae, Filoviridae, Hepadnaviridae, Paramyxoviridae, Flavivirdae, Picronaviridae, and/or Polyomaviridae. Preferably, an MVP is assembled from proteins derived from one viral source. An example of MVP assembled from one viral source is MMV MVP assembled from a natural or recombinant MMV VP2 capsid protein. Alternatively, an MVP could assemble from protein derived from multiple viral sources. An example of MVP assembled from more than one viral protein source is XMuLV MVP assembled from natural or recombinant XMuLV gag protein and natural or recombinant HIV env protein.

In the present invention, the term "species of MVP" refers to all MVP's comprised of the same protein(s) and having the same copy number of those protein(s). For example, a species of MVP is all MVP's comprising 60 copies of the MMV MVP2 protein. In a further preferred definition of a species of MVP, the recombinant forms of a protein are to be considered the same as the natural protein from which it was derived. For example, MVP comprising 60 copies of recombinant MMV VP2 protein is the same species as MVP comprising 60 copies of naturally derived MMV VP2 protein.

Preferably, the act of adding MVP to a solution refers to the addition of only one species of MVP to a solution. Alternatively, the act of adding MVP to a solution refers to the addition of a second species of MVP to a solution. Preferably, in these instances the first species and second species of MVP are added to solution at the same time. Alternatively, in these instances the first species and second species of MVP are added sequentially. One example of adding two species of MVP to a solution sequentially is adding MMV MVP to a solution first and then XMuLV MVP to the same solution second. An example of adding two species of MVP to a solution at the same time is adding a solution that contains both MMV MVP and XMuLV MVP to another solution. In other instances, the act of adding MVP to a solution refers to the addition of two or more species of MVP to a solution.

Preferably, adding MVP to a solution refers to adding a volume of solution which contains a certain species of MVP to another solution which does not contain that certain species of MVP. In the present invention the solution which does not contain a certain species of MVP until that species of MVP is added to it is referred to as a "process solution". For example, a solution of MMV MVP is added to a CHO cell supernatant process solution which does not contain MMV MVP. In another example, a solution of XMuLV MVP is added to a CHO cell supernatant process solution which contains MMV MVP but not yet XMuLV MVP. In the present invention, the solution containing MVP which is added to the process solution can be referred to as a "stock solution of MVP", or "MVP stock solution". Preferably, unlike stock solutions of non-infectious particles common to the art, stock solutions of MVP will have known concentrations of MVP. For example, stock solutions of MVP contained within the kit embodiments of this invention will include MVP concentration information. Moreover, a stock solution of MVP has a higher concentration of MVP than other non-infectious particles common to the art. For example, MVP in a stock solution may be present at concentrations of at least $1\times10$ MVP/ml, $1\times10^6$ MVP/ml, $1\times10^7$ MVP/ml, $1\times10^8$ MVP/ml, $1\times10^9$ MVP/ml, $1\times10^{10}$ MVP/ml, $1\times10^{11}$ MVP/ml, $1\times10^{12}$ MVP/ml, $1\times10^{13}$ MVP/ml, $1\times10^{14}$ MVP/ml, $1\times10^{15}$ MVP/ml, $1\times10^{16}$ MVP/ml, or greater. In addition, MVP stock solutions will contain MVP at purities higher than other non-infectious particles common to the art. For example, non-MVP related proteins in a stock solution of MVP may be less than 65% of all the proteins in the solution, less than 55% of all the proteins in the solution, less than 45% of all the proteins in the solution, less than 35% of all the proteins in the solution, less than 25% of all the proteins in the solution, less than 15% of all the proteins in the solution, less than 5% of all the proteins in the solution. Purity of MVP in a stock solution can be determined through methods common to the art including, but not limited to, Polyacrylamide Gel Electrophoresis (PAGE), high pressure liquid chromatography, mass spectroscopy, flow cytometry, ELISA, dynamic light scattering, gel filtration, or ultracentrifugation. Examples of producing stock solutions of MVP are described in the examples section. Preferably, a stock solution of MVP contains one species of MVP. One example of a MVP stock solution containing one species of MVP is an MVP stock solution containing MMV MVP. Alternatively, a stock solution of MVP can contain multiple species of MVP. One example of a MVP stock solution containing multiple species of MVP is a stock solution containing MMV MVP and XMuLV MVP.

The quantity of MVP stock solution added to a process solution will vary depending on several factors including but not limited to, the volume of process solution, the desired percent (v/v) of MVP stock solution in the process solution after addition, and the concentration of MVP in the MVP stock solution. Preferably, the volume of an MVP stock solution addition may be in the order of milliliters or microliters. For example, the volume of addition may be about 100 microliters or less, about 200 microliters or less, about 500 microliters or less, about 1 milliliter or less, about 2 milliliters or less, about 5 milliliters or less, about 10 milliliters or less, about 100 milliters or less, or about 1000 milliliters or less. Alternatively, the volume of addition may be liters. For example, the volume of addition may be about 1 liter or less, about 2 liters or less, about 5 liters or less, or about 10 liters or less. Preferably, after addition, the percent of MVP stock solution within a process solution may be about less than 1% (v/v) or less, about 2% (v/v) or less, about 3% (v/v) or less, about 4% (v/v) or less, about 5% (v/v) or less, about 10% (v/v) or less, about 25% (v/v) or less, or about 50% (v/v) or less.

Preferably, the process solution contains a biologic of interest. In the present invention, the term "biologic of interest" refers to any molecule produced by means of a biological process that may exhibit therapeutic potential. One example of a biological process in the present invention is cellular protein expression. In some cases, biologics of interest can be composed of sugars, proteins, nucleic acids or complex combinations of these substances. In other cases, a biologic of interest may be living entities such as cells and/or tissues. Preferably, a biologic of interest is an antibody, a non-antibody protein, a vaccine, a nucleic acid, or a blood or plasma derivatives. An example of an antibody as a biologic of interest is Trastuzuman, which is marketed under the trade name Herceptin™. Another example is Rituximab, marketed under the trade name Rituxan™. Another example is bevacizumab, marketed under the trade name Avastin™. Examples of a non-antibody proteins as biologics of interest include, but are not limited to, granulocyte colony stimulating factor (GCSF), a stem cell factor, leptin, a hormone, a cytokine, a hentatopoietic factor, a growth factor, an antiobesity factor, a trophic factor, an anti-inflammatory factor, a receptor, a soluble receptor, enzyme, and/or a variant, a derivative, or an analog of any of these proteins. Other preferred examples of biologics of interest include but are not limited to insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), a motilin, an interferon (e.g., alpha, beta, or gamma), an interlenkin (e.g., IL-1, IL-2, IL-3, IL-4, IL-5, IL-6, IL-7, IL-8, IL-9, IL-10, IL-11 and/or IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), a fibroblast growth factor (FGF), neurotrophic growth factor (NGF), a bone growth factor such as, for example, osteoprotegerin (OPG), an insulin-like growth factor (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin platelet-derived growth factor (PGDF), a colony stimulating growth factor (CSFs), bone morphogenetic protein (BMP), superoxide dismutase (SOD), tissue plasminogen activator (TPA), urokinase, streptokinase, or kallikrein, and/or a variant, derivative, or an analog of any of these proteins. One preferred example of a vaccine as biologic of interest is Recombivax HB. Another preferred example of a vaccine is Gardasil. Another preferred example of a vaccine is Optaflu. Another preferred example is Cervarix. One preferred example of a nucleic acid as a biologic of interest is fomivirsen, which is marketed under the trade name Vitravere™. Another preferred example of a nucleic acid is mipomersen, which is marketed under the trade name Kynantro™. Another preferred example is Pegaptanib, which is marketed under the trade name Macugen™. One preferred example of a blood or plasma derivate as a biologic of interest is albumin. Another preferred example of a blood or plasma derivative is antihemophilic factor. Another preferred example is antihemophilic factor/von willebrand factor complex. Other preferred examples of biologics of interest in the present invention include but are not limited to anti-inhibitor coagulant complex antithrombin (recombinant), c1 esterase inhibitor, coagulation factor, corifact, fibrin, fibrinogen, immune globulin, profilnine SD—factor IX complex, kcentra (Prothrombin Complex Concentrate, Human), protein C concentrate (Human), thrombin, bone marrow products, and embryonic fluid products.

Preferably, the biologic of interest in a process solution has been produced by a cell culture process or a fermentation process. In the present invention, the term "cell culture expression process" refers to a process by which cells are grown under controlled conditions to express a certain gene(s) (typically introduced in vitro). In the present invention, the term "fermentation expression process" refers to a process by which microorganisms are conditioned to grow and express a certain gene(s) (typically introduced in vitro). Preferably, cell lines for cell culture or fermentation expression are of human animal, plant, insect, hybridoma, yeast, or bacteria origin. Examples of human cell lines include but are not limited to, HeLa, NCI60, DU145, MCF-7, PC3, ARH-77, and/or HEK-293 cells. Examples of animal cell lines include but are not limited to, CHO, BHK, NSO, MDCK, Vero, GH3, PC12, and/or MC3T3 cells. Examples of plant cell lines include but are not limited to, Tobacco BY-2 cells. Examples of insect cell lines include but are not limited to, sf9, High Five, and/or C6/36 cells. Examples of yeast species from which yeast cell lines can be from include but are not limited to, *Saccharomyces cerevisiae* and/or *Pichia pastoris* cells. Examples of bacteria species from which bacterial cell lines can be from include but are not limited to, *Escherichia coli* and/or *Lactobacillus*. Alternatively, cell lines for cell culture or fermentation expression are of other origins. Examples of other cell lines include but are not limited to, ZF4, AB9, and/or *Xenopus* A6 kidney epithelial cells.

In the present invention, the term "hybridoma" refers to a cell that is produced in the laboratory from the fusion of an antibody-producing lymphocyte and a non-antibody-producing cancer cell, preferably a myeloma or lymphoma. Moreover, hybridomas of the present invention are capable of proliferating and producing a continuous supply of specific monoclonal antibody. Examples of hybridoma cell lines include but are not limited to, RFT5, SP2/o cells, and/or HB54 cells.

In some instances, cell culture or fermentation processes which express biologics of interest co-express other biologics or molecules. In the present invention, all biologics or molecules that are co-expressed during a cell culture or fermentation process that are not biologics of interest are referred to as "impurities". Examples of impurities include but are not limited to, host cell proteins (proteins expressed other than the biologic of interest), nucleic acids (besides a nucleic acid that is a biologic of interest), charge variants of the biologic of interest, aggregate complexes, Beta-glucans, and/or virus. Additionally, impurities refer to all biologics, molecules, or chemicals that are added to a solution containing a biologic of interest. Therefore, one example of an impurity is MVP after it has been added to a process solution. In some instances a process solution may exist in the original cell culture or fermentation expression solution along with all originating impurities. In other instances this solution may have been purified from its original state, prior to the addition of MVP, through a variety of techniques commonly known in the art as "purification techniques". In the present invention, the term "purify" refers to an act of reducing the amount of impurities present in solution relative to the amount of a non-impurity present in the same solution. Preferably, a non-impurity refers to biologic of interest present in the solution. Examples of purification techniques which may have purified the process solution prior to the addition of MVP including but are not limited to, centrifugation, chromatography, filtration, precipitation, concentration, diafiltration, pasteurization, or viral inactivation. In some instances, the solution may have been subjected to other techniques or rigors including but not limited to, freezing, thawing, pH adjustment, and/or dilution prior to the addition of MVP.

The first embodiment of the present invention involves "processing the solution through a purification technique". In this step of the method, the term "solution" refers to the process solution after a quantity of MVP stock solution has been added to it. Preferably, this solution contains a biologic of interest. As previously mentioned, non-biologics of interest, "impurities" may also be present, including MVP. During the first embodiment of the present invention, this solution is "process[ed] . . . through a purification technique". In the present invention, the term "purification technique" refers to techniques which "purify" the solution, that is, techniques which reduce the amount of impurities present in solution relative to the amount of a non-impurity present in the same solution. Preferably, a non-impurity refers to a biologic of interest. Thus, a further preferred embodiment of the present invention is to purify a biologic of interest present in the process solution through an act of processing that solution through a purification technique.

Preferably, the purification technique used to process the process solution is a chromatography, filtration, ultrafiltration, centrifugation, or viral inactivation technique. In the present invention, chromatography, filtration, ultrafiltration, or centrifugation can be referred to as "separation techniques". Separation techniques are methods of mass transfer that distribute the constituents of a solution into two or more distinct solutions. Separation techniques are carried out based on differences in physical and chemical properties between the various components of a solution, including but not limited to, size, shape, mass, and/or chemical affinity. Examples of separation techniques include but are not limited to, affinity chromatography, ion-exchange chromatography, hydrophobic interaction chromatography, reverse phase chromatography, mixed mode chromatography, depth filtration, size based filtration (including nanofiltration, sterile filtration, or ultrafiltration), and centrifugation. Viral inactivation techniques refer to any method aimed at reducing the abilities of virus to retain its proper structure or replicate. Examples of viral inactivation techniques include exposure to solvent and detergent or chemical treatments, low pH, heat, or ultraviolet radiation.

The first embodiment of the present invention involves "processing the solution through a purification technique". In the present invention, the term "processing" refers to the act of physically performing a purification technique. Different physical acts of processing a separation technique include, but are not limited to, pumping, applying direct pressure, centrifugation, gravity, or shaking. In some instances, more than one way of processing may apply for one separation technique, depending on the format of the separation technique. For example, the format of an ion exchange chromatography technique may be a packed column, filter, or 96 well plate. Therefore the act of processing this ion exchange chromatography technique may consist of pumping, applying pressure, centrifugating, gravity, and/or shaking Different physical acts of processing a viral inactivation technique include, but are not limited to, adding organic solvents, detergents or acidic solutions, microwaving, exposing to UV light, immersion in hot water bath, pasteurization, or steam treatment.

In some cases, processing a solution through a separation technique reduces the amount impurities in solution and is therefore said to "purify" the solution. After addition of MVP to a process solution, MVP is considered an impurity. Preferably, the quantity of MVP present in the process solution is reduced through the act of processing, as compared to the quantity of MVP present before such processing. Alternatively, the quantity of MVP present in the process solution is not reduced through processing. The ability of a purification technique to reduce the amounts of impurities in a solution relies on a set of parameters, or "variable inputs", that someone skilled in the art utilizes to process. Examples of variable inputs include but are not limited to; pH, conductivity, and temperature of the solution to be processed. Other examples of variable inputs include but are not limited to, pressure applied, exposure time, or flow rate of a solution. Another example is the concentration of constituents in the solution. Other examples are pH, conductivity, or chemical composition of buffers used to process a solution. Another example is the criteria used for collecting the process solution during or after the act of processing. Thus, the set of parameters utilized to process a solution through a purification technique impacts the effectiveness of the techniques' ability to reduce impurities (such as MVP) relative to non impurities (such as biologics of interest).

In some cases, an effective criteria for collecting process solution during or after processing is employed which results in fewer impurities. Once the act of processing has begun, the methodology of collecting process solution(s) relies on someone skilled in the art. In the present invention, a process solution which has been collected since the act of processing has begun is referred to as "process collections". Examples of methodologies used to collect process collection during a purification technique include but are not limited to, light absorbance detection and fixed volume. Preferably, someone skilled in the art will utilize an effective collection criteria during or after processing so that a process collection contains less impurities that the process solution did before processing. Even more preferably, a collection criteria is utilized so that a process collection contains less MVP than the process solution prior to processing.

In some cases, distinct process collections are collected during processing. One example of how a distinct process collection is collected during processing is a collection of column effluent during the loading phase of a chromatography separation technique. Another example would be collecting the column effluent during the wash phase of a chromatography separation technique. Another example would be collecting the column effluent during the elution phase of a chromatography separation technique. Another example would be collecting the filtrate of a filter. Another example would be collecting the solution during low pH titration. Another example would be collecting the solution during exposure to UV light or chemical treatment. Alternatively, distinct process collections may be collected after processing. One example of how distinct processed solutions are collected after processing is by collecting the column effluent during the strip phase of a chromatography separation technique. Another example would be collecting the solution after low pH titration followed by an increase in pH and filtration. Another example would be collecting the solution after exposure to UV light or chemical treatment.

The first embodiment of the present invention involves "quantifying the amount of MVP removed from the solution". In this specific embodiment, the act of "quantifying" refers to the means by which someone skilled in the art mathematically calculates the amount of MVP removed from processing the solution. Preferably, this value may be expressed as a log reduction value (LRV). Alternatively this value may be expressed as a molarity (mol/L), in total grams of MVP, and/or in total molecules of MVP. Preferably, someone skilled in the art could mathematically calculate the amount of MVP removed from the solution by an equation relating the amount of MVP remaining in solution after processing to the amount of MVP in solution prior to processing. Preferably, the quantity of MVP present in solution prior to processing is known by multiplying the volume of an MVP stock solution added to a process solution by the MVP concentration of that MVP stock solution. Even more preferably, the quantity of MVP present in solution prior to processing could be determined empirically. Likewise, preferably, the quantity of MVP remaining in a process collection could be determined empirically. Different techniques can be utilized for determining the amount of MVP present in solution empirically. In this present invention, these techniques will be referred to as "quantification techniques". Preferred examples of how to quantify the amount of MVP removed from solution are shown in the examples section.

Preferably, "quantification techniques" used for empirically determining the amount of MVP in a solution include ELISA, PCR, nanoimaging, fluorescence, enzymatic, microscopy, spectrophotometry, transmission electron microscopy (TEM), and western blot techniques. In this embodiment of the present invention, the "solution" from which the amount of MVP is being determined, refers to a process solution after an addition of MVP, a process collection(s), or aliquots taken of either. In this embodiment, the solution can be referred to as "an MVP containing solution". Preferably, when performing a quantification technique, a solution which contains an agent capable of binding to a MVP or to a molecule attached to a MVP, is added to an MVP-containing solution. One example of such an agent is an antibody. Alternatively, when performing a quantification technique, a solution which contains PCR primers capable of binding to an in vitro nucleic acid or to a nucleic acid sequence bound to a molecule which can be first bound to a MVP, is added to an MVP containing solution. In the present invention the solution containing an agent or PCR primer is referred to as "a quantification solution".

Preferably, during the act of quantifying the amount of MVP in a solution, a serial dilution of MVP in process solution will be made and analyzed via a quantification technique. Preferably, the data from such analysis will relate the quantity of MVP in a solution to a signal received as a result of the quantification technique. Examples of signals received as part of a quantification technique include, but are not limited to, Ocular Density (OD), Absorbance Units, pRNA copies per ml, pDNA, copies per ml, RNA copies per ml, DNA copies per ml, or units of reverse transcriptase activity. Even more preferably, a line of best fit will be used in conjunction with the data to relate quantification technique signals generated by unknown quantities of MVP to signals generated by known quantities. Examples of making and using serial dilutions to quantify the amount of MVP in solution in lieu of quantifying MVP removal from a solution are shown in the examples section.

In some cases a MVP will be composed of natural or recombinant viral capsid or envelope protein and display epitopes or heterologous epitopes on its surface. Preferably, in these instances, antibodies that bind to these epitopes or heterologous epitopes can be utilized during a quantification technique to determine the amount of MVP present in solution. One example of how an antibody binding to an epitope displayed on an MVP could be utilized to determine the amount of MVP is by adding anti-VP2 antibody directed against a natural or recombinant VP2 capsid protein to an MMV MVP containing solution during an ELISA quantification technique. An example of how an antibody binding to a heterologous epitope displayed on an MVP could be utilized to determine the amount of MVP is by adding an anti-his antibody directed against a his tag (present as a heterologous epitope on the surface of the MVP) to an MVP containing solution during an ELISA quantification technique. Preferably, antibodies known in the art to be capable of binding to epitopes or heterologous epitopes contained by a MVP can be the agent used in a quantification solution. Even more preferably, novel antibodies made by using MVP as an immunogen in an organism can be the agent used in a quantification solution. Thus surprisingly sensitive quantification measurements and MVP removal calculations can be achieved through non-genetic material based techniques common to the art.

In other cases a MVP will be bound to a linker molecule. Preferably, in these instances, antibodies that bind to linker molecules can be added to an MVP containing solution during a quantification technique to determine the amount of MVP present in solution. In other cases, a solution containing a molecule can be added to an MVP containing solution prior to addition of a quantification solution. In the present invention, the term "molecule" refers to a natural or artificial small molecule or protein which has an affinity for a MVP.

In some cases, molecules are added to MVP-containing solution to form a MVP-molecule complex. Preferably, in these cases, molecules do not have nucleic acid sequences attached and displayed on their surface. In other cases, molecules may have nucleic acid sequences attached and displayed on their surface. Preferably, in instances when a solution containing a molecule is added to an MVP containing solution, a quantification solution is then added to determine the amount of MVP present in solution via a quantification technique. One example of how the amount of MVP present in solution is determined by adding a solution containing a molecule is by first adding a solution containing streptactin to a solution containing strep tag-MVP (MVP comprising a strep tag heterologous epitope) and then using an anti-streptactin antibody to determine the amount of MVP with an ELISA quantification technique. Another example is by first adding a solution of nucleic acid-conjugated streptactin (streptactin containing an attached segment of nucleic acid) to a MVP containing solution and then using primers directed against the segment of nucleic acid to determine the amount of MVP with a PCR quantification technique.

In some cases, a MVP will contain within its structure a segment of in vitro nucleic acid. Preferably, in these instances, a quantification solution containing primers that bind to in vitro nucleic acid contained within the MVP can be utilized to determine the amount of MVP with a PCR quantification technique. In some instances methods of enhancing signals generated by quantification techniques common to the art may be used. One example of a method of enhancing signals generated by quantification techniques involves metal enhanced luminescence.

Preferably, quantifying the amount of MVP removed refers to one species of MVP. Preferably, in these instances, one species of MVP was added to a process solution which was processed through a purification technique. Alternatively, in instances where two or more species of MVP are added to a process solution which is processed through a purification technique, quantifying the amount of MVP removed may refer to multiple species of MVP. Preferably, in these instances, the same quantification techniques may be used in determining the amounts of multiple species of MVP in a solution. One example of using the same quantification technique in determining the amounts of multiple species of MVP in a solution is using an anti-VP2 antibody which binds to MMV MVP and an anti-env antibody which binds to XMuLV MVP in separate ELISA quantification techniques. Alternatively, different quantification techniques may be used in determining the amounts of multiple species of MVP in a solution One example of using different quantification techniques is using an ELISA based technique to determine the amount of MMV MVP in solution and using a PCR technique used to determine XMuLV MVP in the same solution.

Preferably, the steps of adding MVP to a solution, processing the solution through a purification technique, and quantifying the amount of MVP removed from solution are to be performed sequentially and un-interrupted. Alternatively, additional steps may be included according to rational experimental design. Examples of additional steps that may be included according to rational experimental design include but are not limited to, further purifying the stock solution of MVP prior to adding it to a process solution (via filtering, chromatography, or other techniques), performing dialysis or diafiltration on the stock solution of MVP prior to adding it to a process solution, adding a non-MVP solution to the process solution before or after the addition to MVP. An example of a non-MVP solution is a cell culture suspension of live virus preparation not containing virus. Examples of other additional steps may include taking an aliquot of the process solution after addition of MVP but prior to processing through a purification technique, centrifuging or diluting a process collection or an aliquot of a processed collection prior to performing a quantification technique, and/or freezing and thawing the aliquot taken for a quantification technique prior to performing the quantification technique.

Thus, one embodiment of the present invention is a method of quantifying the amount of MVP removed from a solution. Another embodiment of the invention is a kit used for executing the method. Preferably, the kit will contain one container comprising a stock solution of a single species of MVP and one container comprising a quantification solution. Alternatively, the kit will contain one container comprising a stock solution of MVP which contains multiple species of MVP. Preferably, in this instance, the kit will also contain multiple containers of quantification solution for empirically determining the amount of each species of MVP present in the stock solution bottle. In instances where the kit contains multiple stock solution bottles of MVP (containing different species of MVP), the kit will also contain multiple quantification solution containers for determining the amount of those species of MVP.

In the present invention, the "container comprising a stock solution of MVP refers to a bottle contained within the kit that contains a stock solution of MVP at a known concentration (of MVP). Moreover, the MVP in a stock solution container is present at a concentration and purity that exceeds the concentration and purity levels of other non-infectious particles common to the art. For example, the concentration of an MVP in a stock solution container may be at least $1\times10^5$ MVP/ml, $1\times10^6$ MVP/ml, $1\times10^7$ MVP/ml, $1\times10^8$ MVP/ml, $1\times10^9$ MVP/ml, $1\times10^{10}$ MVP/ml, $1\times10^{11}$ MVP/ml, $1\times10^{12}$ MVP/ml, $1\times10^{13}$ MVP/ml, $1\times10^{14}$ MVP/ml, $1\times10^{15}$ MVP/ml, $1\times10^{16}$ MVP/ml, or greater and the non-MVP related proteins may be present at levels less than 65% of all the proteins in the solution, less than 55% of all the proteins in the solution, less than 45% of all the proteins in the solution, less than 35% of all the proteins in the solution, less than 25% of all the proteins in the solution, less than 15% of all the proteins in the solution, less than 5% of all the proteins in the solution. Preferably, the MVP in a stock solution bottle may be in the original cell culture or fermentation based expression solution from which the MVP assembled. Even more preferably, the MVP in a stock solution is purified so that concentrations of cellular non-MVP related proteins, nucleic acids, or lipids in solution are reduced as compared to the original expression solution from which the MVP assembled. Even more preferably, the MVP in a stock solution bottle is highly purified from the original expression solution from which the MVP assembled. In some instances, a stock solution of MVP may contain added buffer components. Preferably, a single stock solution bottle of MVP contains only one specific species of MVP. Alternatively, a single stock solution bottle contains multiple species of MVP.

In the present invention, the "container comprising a quantification solution" refers to a bottle contained within the kit that comprises a quantification solution containing an agent capable of binding to a MVP, an in vitro nucleic acid, a molecule attached to MVP, or a nucleic acid sequence bound to that molecule. Preferably, a quantification bottle comprises a quantification solution containing an antibody capable of binding to MVP or to a molecule which can be bound to an MVP. One example of a quantification bottle comprising a quantification solution containing an antibody is a quantification solution bottle, comprising a quantification solution containing anti-VP2 antibody which can be utilized during an ELISA quantification technique to determine the amount of MMV MVP in a solution. In these instances, the antibody may bind to epitopes or heterologous epitopes present on the MVP or epitopes present on the molecule. In an even further preferred embodiment of the invention, the kit also contains a solution of a secondary antibody capable of binding to the primary antibody which binds to MVP or a molecule bound to MVP. Preferably, the solution of secondary antibody is added during the execution of a quantification technique after the addition of antibody capable of binding to MVP or molecule.

In some instances, an antibody which can bind to an MVP or a molecule bound to an MVP is not conjugated to an enzyme. Alternatively, in a further preferred embodiment of the present invention, an antibody contained in a quantification solution which is capable of binding to MVP or to a molecule bound to a MVP is conjugated to an enzyme. Examples of enzymes which can be conjugated to antibodies are horse radish peroxidase (HRP) and alkaline phosphatase. Likewise, in another further preferred embodiment, a secondary antibody which binds to an antibody capable of binding to an MVP or a molecule bound to an MVP is conjugated to an enzyme.

In a further preferred embodiment of the invention, the kit further comprises an ELISA plate containing an immobilized antibody or molecule that binds to MVP. Preferably, the plate contains 96 wells. Alternatively the plate may contain less than 96 wells. Preferably, the immobilized antibody or molecule contained in the ELISA plate bind to the MVP contained within the MVP stock solution of the same kit.

Alternatively, in another further preferred embodiment, the quantification bottle comprises a quantification solution containing primers capable of binding to an in vitro nucleic acid sequence or to a segment of nucleic acid bound to a molecule which can be bound to a MVP. Preferably, in these instances, a quantification solution bottle may contain PCR primers specific to a segment of in vitro nucleic acid contained within MVP. Alternatively, in these instances, a quantification solution bottle may contain PCR primers specific to a segment of nucleic acid that is adhered to a molecule that may be first bound to a MVP during the step of quantification.

in a further preferred embodiment of the present invention, the kit further comprises a solution of a molecule which can bind to MVP. One example of a solution of a molecule is a solution containing streptavidin. Another example of a solution of a molecule is a solution containing streptavidin displaying a short nucleic acid sequence. Preferably this solution will be added during execution of a quantification technique prior to the addition of a quantification solution.

In a further preferred embodiment of the invention, additional reagents for performing ELISA or PCR are included in the kit. Examples of additional reagents for performing ELISA or PCR include common buffers, enzymes, or molecules common to the art.

Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

EXAMPLES

Example 1

Figure 2:
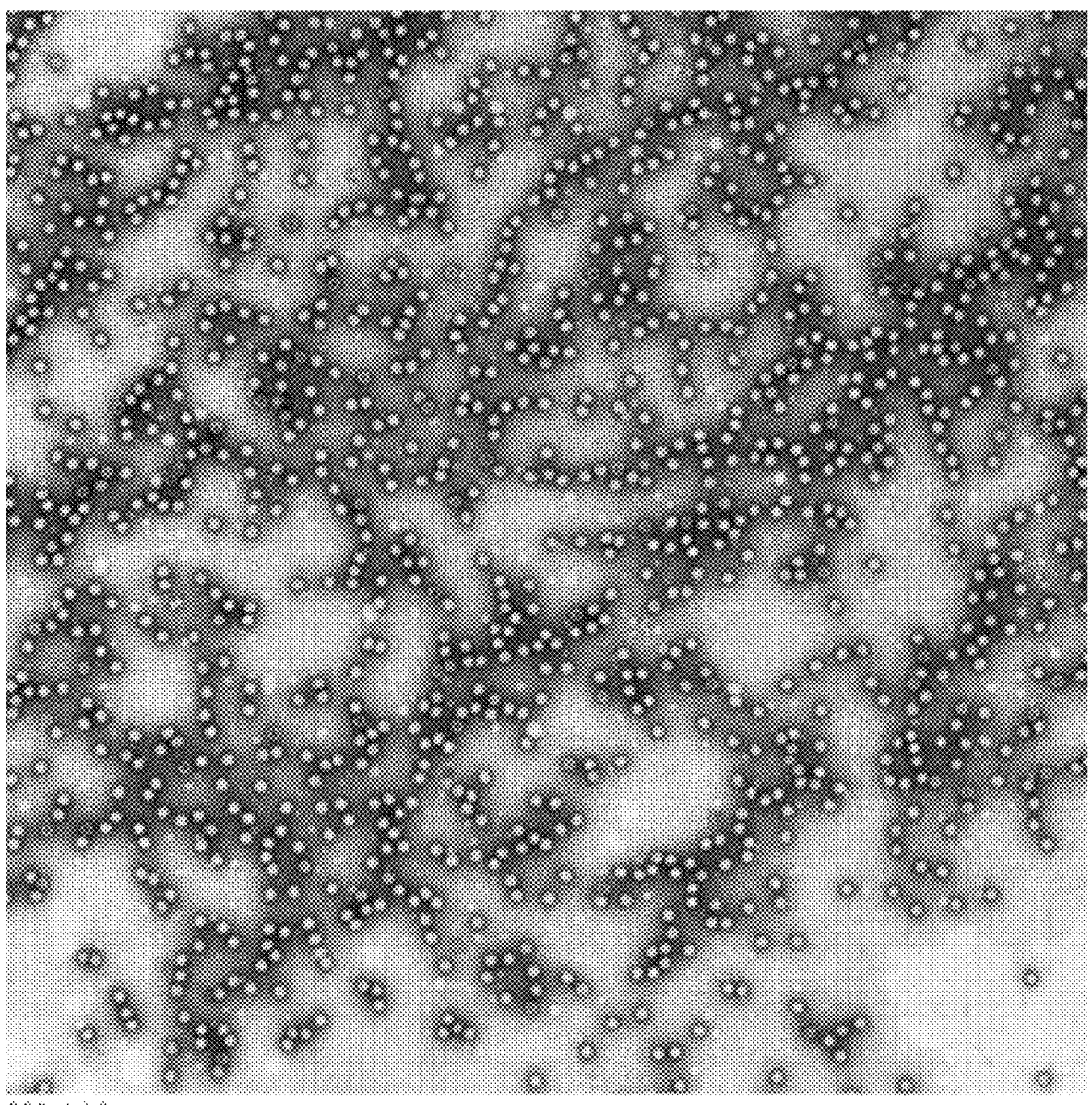
FIG. 2: Transmission electron microscopy image of MMV MVP stock solution.

Cloning, Expressing and Purifying Mouse Minute Virus (MMV) Mock Virus Particles (MVP) to Produce a Stock Solution Mouse minute virus (MMV) is a single-stranded DNA containing virus belonging to the family Parvoviridae that infects vertebrate hosts. The mouse minute virus capsid protein gene, VP2, can be cloned and expressed using a baculovirus expression system to generate MVP (Hernando, 2000). In order to clone and express MMV MVP, the capsid protein gene VP2 was synthesized from a published MMV VP2 sequence template (GenBank J02275.1, nucleotides 2794-4557, SEQ ID No.4). Certain codons were optimized during this synthesis to increase the efficiency of translation (SEQ ID No. 5). The resulting amino acid sequence (SEQ ID No. 6) was 100% homologous to the published VP2 sequence (GenBank AAA67114.1, SEQ ID No. 7). The gene was inserted into a cloning vector, pUC57 from which it was then subcloned into a pFastBac expression vector. This vector was then used to transform DH10Bac cells. After screening for positive clones, bacmid DNA was used to transfect Sf9 cells. Recombinant baculovirus carrying MMV VP2 gene was collected from Sf9 cell culture supernatant. The original recombinant baculovirus stock was then amplified and was collected at 4 days post infection. This stock was cultivated in Grace's medium supplemented with 10% FBS and was then used to transfect Sf9 cells at a multiplicity of infection of 4.0. Cells were then harvested at 3 days post-infection and resuspended in lysis buffer. This suspension was then frozen and thawed 3 times. Soluble lysate was recovered by centrifugation and then purification of the resulting MVPs was performed following a published protocol (Hernando, 2000). The purity of MVP after Cesium Chloride density gradient fractionization was determined through SDS-PAGE with Coomassie blue staining (FIG. 1) and western blot analysis (not shown). Based on the results, fractions were pooled to form MMV MVP stock solution. A visualization of MMV MVP stock solution and a concentration determination were made through transmission electron microscopy with negative staining (FIG. 2).

Example 2

Figure 3:
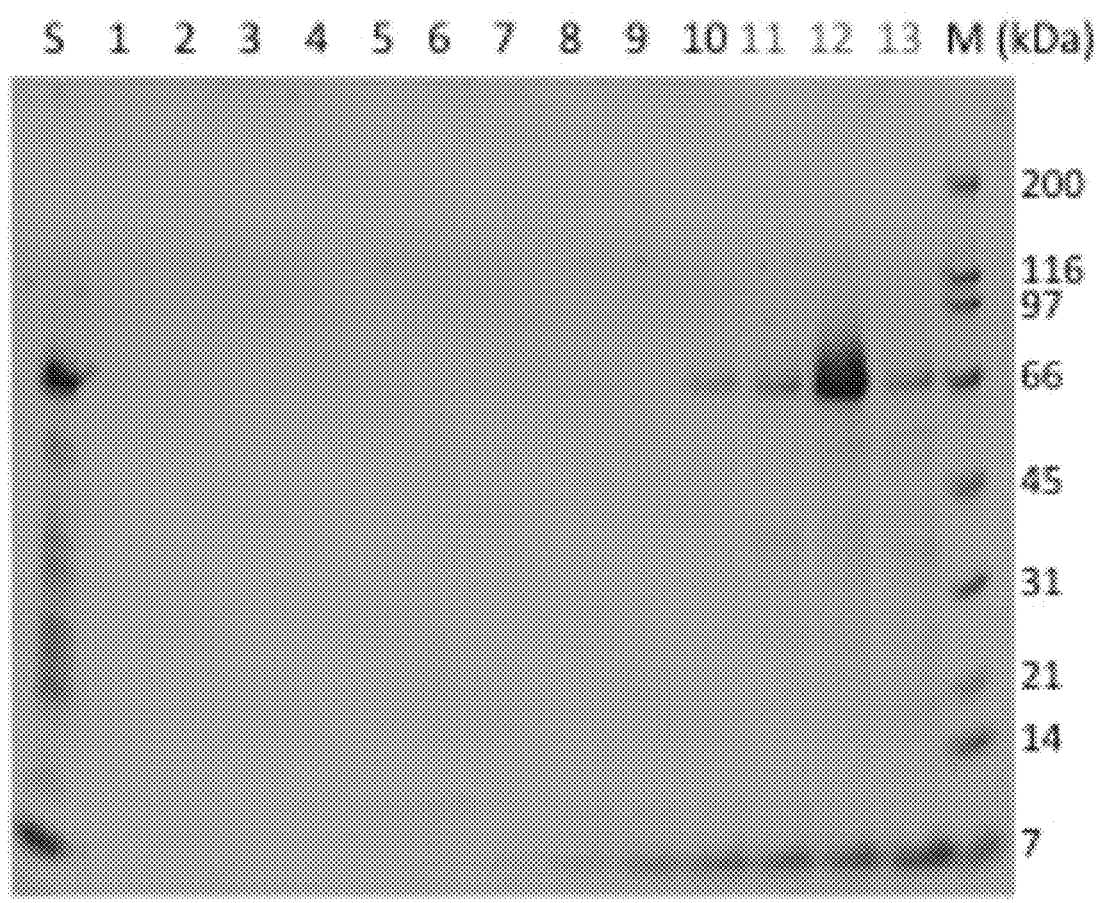
FIG. 3: Purity of heterologous epitope MMV MVP fractions.
Figure 4:
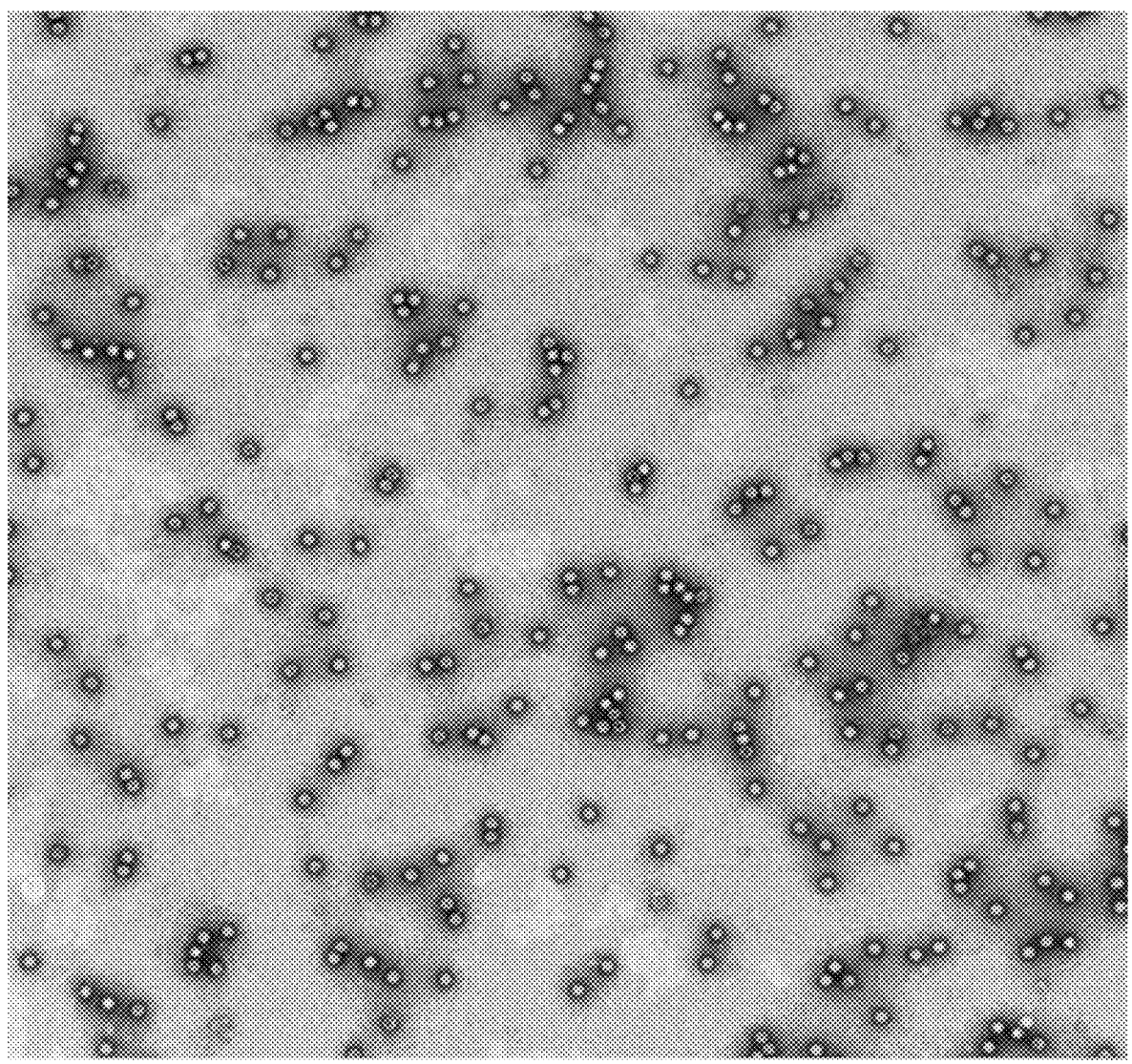
FIG. 4: Transmission electron microscopy image of heterologous epitope MMV MVP stock solution.

Cloning, Expressing and Purifying Heterologous Epitope MMV MVP to Produce a Stock Solution MMV MW's can be made to display heterologous epitope (s) on the surface of its structure and could thus be used as a target for MVP quantification. In order to clone MMV MVP displaying a heterologous epitope, the natural nucleotide sequence of the MMV VP2 gene was first synthesized (using GenBank J02275.1, nucleotides 2794-4557, SEQ ID No.4 as a template) while optimizing certain codons to increase the efficiency of translation (SEQ ID No. 5). This sequence then underwent mutagenesis (SEQ ID No. 8), at amino acid position 2, resulting in an amino acid sequence which included the insertion of a 10 amino acid sequence containing a strep II tag (SEQ ID No. 9). The same methods and procedures were then utilized from example 1 to clone, express, purify and produce heterologous epitope (strep II tag) containing MVP stock solution. The purity of MVP after Cesium Chloride density gradient fractionization was determined through SDS-PAGE with Coomassie blue staining (FIG. 3) and western blot analysis (not shown). Based on the results, fractions were pooled to form heterologous epitope MMV MVP stock solution. A visualization of the resulting stock solution and a concentration determination were made through transmission electron microscopy with negative staining (FIG. 4). Further validation that the resulting MVP displayed strep II tag was made through an ELISA assay which utilized streptactin and mAb against the tag (data not shown).

Example 3

Cloning, Expressing and Purifying a Xentropic Murine Leukemia Virus (XMuLV) MVP to Produce a Stock Solution It has been shown previously that the infection of cells with Ad5 vectors that co-express XMRV env and gag genes lead to the production of non-infectious particles (Makarova, 2011). First, the XMulV gag and env genes can be custom synthesized using the published sequences of the genes as templates (GenBank accession number JF908817.1, nucleotides 546-2156, SEQ ID No. 10, and accession number K02730.1, nucleotides 291-2225, SEQ ID No. 11, respectively). Then the nucleic acid sequences could be cloned into pUC57 vectors. Next, the env sequence can be sub-cloned into CMV-driven expression cassette of pDP1 Shuttle vector and the gag sequence could be cloned into the MCMV-driven expression cassette of the same vector resulting in pDP1-XMuLVenvgag. The pDP1-XMuLVenvgag plasmid could then be linearized and mixed with the pAdEasy-1 plasmid before co-transfecting 293-AD cells to produce recombinant Ad5-XMuLV. The recombinant adenovirus could be purified by double centrifugation on cesium chloride gradients. To produce an MVP stock solution, Mv1Lu cells can be infected with Ads-XMuLV for virus absorption. Culture media could then be collected after 48 hours of infection, passed through a 0.45-mm filter, and concentrated/purified by ultracentrifugation through a sucrose gradient.

Example 4

Cloning, Expressing and Purifying XMuLV MVP Containing Heterologous Epitopes to Produce Stock Solution XMuLV MVP's can be made to contain heterologous epitope(s) on the surface of its structure through methods discussed in Suomalainen et al., 1994. Alternatively, the nucleotide sequences of either the XMuLV gag and/or env gene (GenBank accession number JF908817.1, nucleotides 546-2156, SEQ ID No. 10, and accession number K02730.1, nucleotides 291-2225, SEQ ID No. 11, respectively) could be synthesized to include the sequence for a heterologous tag such as, but not restricted to, astrep-tag (amino acid sequence WSHPQFEK (SEQ ID No:1)), a Flag tag (amino acid sequence DYKDDDDK (SEQ ID No:2)) or a His-tag (amino acid sequence HHHHHH (SEQ ID No:3)). Cloning, expression, and purification could occur as described in Example 3 above.

Example 5

Assembling XMuLV MVP Containing a Nucleic Acid

In order to generate XMuLV MVP containing a piece of nucleic acid, XMuLV gag- and/or env protein can first be expressed from mammalian cell as described in the example 4. In vitro assembly of XMuLV gag and/or env protein to include nucleic acid, which could be DNA or RNA, can then be carried out following published protocols (Gross et al., 1997; Yu et al., 2001).

Example 6

Quantifying the Removal of MMV MVP from a mAb Containing Solution After Processing Through an Anion Exchange Column NS0 harvest cell culture fluid containing a monoclonal antibody (mAb1) was thawed from storage −80 degrees Celsius. The material was titrated to a pH of 7.5 with 1 M Tris and then filtered through a 0.22 μm filter. One hundred microliters of MMV MVP stock solution (at a concentration of $1 \times 10^9$ MVP/ml) comprising 60 copies of VP2 capsid protein displaying a heterologous strep II tag epitope was added to 10 mls of the mAb1 process solution (1% v/v addition). The process solution thus had a concentration of $9.9 \times 10^6$ MVP/ml ($(0.1\ ml \times 1 \times 10^9\ MVP/ml)/10.1\ mls$) Next, a 0.66 cm×2 cm Q Sepharose Fast Flow column was packed to vendor recommended specifications (GE healthcare) and equilibrated with 50 mM Tris-HCl, 50 mM NaCl (pH 7.5) at a flow rate of 60 cm/hr using an AKTA explorer. After equilibration, the 10.1 mls of process solution containing MVP was loaded through the column at 60 cm/hr. Process collections were taken as the $UV_{280}$ trace indicated flow through of protein. 200 ul samples of the collections were taken.

An ELISA quantification technique was then performed to quantify the amount of MVP removed in each of the process collections from purification processing. Microtiter wells were first coated with rabbit polyclonal anti-MMV VP2 antibody (Alpha Diagnostic, Cat #MVMVP21-S). 50 uls of each of the process collection samples were added to the coated wells, incubated for 1 hour and washed three times with 1× Phosphate Buffer Saline (PBS). In addition a serial dilution of the MMV MVP stock solution was made in the original process material resulting in MVP concentration of $1 \times 10^8$ MVP/ml, $1 \times 10^6$ MVP/ml, and $1 \times 10^4$ MVP/ml. 50 uls of each dilution were also added to coated wells, incubated, and washed. Rabbit polyclonal anti-MMV VP2 antibody was then added to each well, incubated for 1 hour and washed 3 times with 1×PBS. HRP-conjugated anti rabbit antibody (1:500) was then added, incubated for an hour, and washed 3 times with 1×PBS. TMB substrate solution was added and the reaction was stopped by addition of stop solution. Optical Density (OD) was measured at 450 nm. The $OD_{450}$ results are shown in Table 2 below.

TABLE 22

$OD_{450}$ measurements from MMV MVP removal study

| Sample | $OD_{450}$ |
|---|---|
| MVP Dilution 1 ($1 \times 10^8$ MVP/ml) | 1.1 |
| MVP Dilution 2 ($1 \times 10^6$ MVP/ml) | 0.9 |
| MVP Dilution 3 ($1 \times 10^4$ MVP/ml) | 0.52 |
| MVP Dilution control (process solution) | 0.03 |
| Process collection 1 | 0.04 |
| Process collection 2 | 0.01 |

A line of best fit was established with the three dilution samples of known concentration (relating $OD_{450}$ and MVP concentration). The equation for this line was:

$$Y = 0.0525 \ln(x) + 0.1235$$

By plugging in the $OD_{450}$ results from the two process collections, the MVP concentrations in those samples were determined. It was thus found empirically that 0 MVP/ml remained in either process collection. Since the limit of detection in this ELISA assay is unknown, the limit is assumed to be lowest concentration of MVP tested ($1 \times 10^4$ MVP/ml). The log reduction value of MMV MVP was calculated from the known amount of MVP in the process solution and the empirically determined amount of MVP remaining in the process collections. This value, $\geq 9.9 \times 10^2$, is therefore the quantity of MVP removed from solution by way of processing that solution through a purification technique.

Example 7

Quantifying the Removal of XMuLV MVP from a Mab Containing Solution After Processing Through a Parvovirus Filter A solution from a biotechnology process that contains a monoclonal antibody can be purified through protein affinity and ion exchange chromatography columns using methods familiar to the art. The solution could be frozen at −80 degrees Celsius for several months and then thawed and filtered through a 0.22 um filter. 12.5 mls of a XMuLV MVP stock solution could then be pippetted into 250 mls of the filtered process solution (5% spike v/v). A 1 ml sample of this MVP added process solution would be taken for later quantification. The process solution (now containing XMuLV MVP) would then be pressurized through a Vpro parvovirus filter at 30 psi and the filtrate would be collected. A 1 ml sample of this filtrate (process collection) would be taken.

A serial dilution of XMuLV MVP in process solution could be prepared with dilutions of MVP at concentrations of $1 \times 10^9$, $1 \times 10^7$, $1 \times 10^5$, and $1 \times 10^3$ MVPs/ml of process solution. 50 uls of each dilution could then be added to microtiter wells coated with antibody against an XMuLV env epitope. The wells would then be incubated for an hour and washed three times with 1×PBS buffer. Next, a HRP conjugated antibody against a different env epitope could be added to each well, incubated for 1 hour and washed 3 times with 1×PBS. TMB substrate solution would then be added and the reaction stopped by addition of stop solution. OD would measured at 450 nm to produce a data curve depicting the relationship between OD and MVP concentration. $OD_{450}$ results could resemble the data in Table 3 below.

TABLE 3

$OD_{450}$ measurements from XMuLV MVP removal study

| Dilution Concentration (MVP/ml) | $OD_{450}$ |
|---|---|
| $1 \times 10^9$ | 1.47 |
| $1 \times 10^7$ | 0.9 |
| $1 \times 10^5$ | 0.56 |
| $1 \times 10^3$ | 0.33 |
| 0 (process solution control) | 0.01 |

The amount of XMuLV MVP removed from processing through the parvovirus filter could be quantified empirically. The 1 ml samples of process solution (after MVP addition) and process collection would be subjected to the same ELISA method described for the serial dilution samples above. The $OD_{450}$ results would be plugged into an equation which bests fits the data from Table 3 to predict the amounts of MVP in solution prior to filtering and after filtering. From this data, the XMuLV MVP LRV could be calculated as described in Example 6 and according to methods common in the art for quantifying virus removal.

The invention claimed is:

1. A kit comprising:
a stock solution comprising a modified Mouse Minute Virus (MMV) Mock Viral Particle (MVP), wherein the MMV MVP is a non-infectious, non-replicating assembled unit comprising a MMV VP2 viral capsid protein comprising an amino acid sequence having at least 99% identity to SEQ ID NO: 6, wherein said stock solution comprises at least $1 \times 10^{10}$ MMV MVP/ml of said MMV MVP and wherein non-MMV MVP proteins are less than 25% of all proteins in the stock solution.

2. The kit of claim 1, wherein said viral capsid protein is produced in a bacterium, yeast, plant, insect cell, animal or human cell.

3. The kit of claim 1, wherein non-MMV MVP proteins are less than 5% of all proteins in the stock solution.

4. The kit of claim 1, wherein the MMV MVP does not comprise a MMV VP1 viral capsid protein.

5. The kit of claim 1, wherein the MMV VP2 viral capsid protein is encoded by a nucleic acid comprising SEQ ID NO: 5.

6. The kit of claim 1, wherein the MMV VP2 capsid protein comprises SEQ ID NO: 6.

7. The kit of claim 1, wherein the kit further comprises an antibody that specifically binds to the MMV VP2 capsid protein comprising an amino acid sequence having at least 99% identity to SEQ ID NO: 6.

8. The kit of claim 6, wherein the kit further comprises an antibody that specifically binds to SEQ ID NO: 6.

* * * * *